United States Patent
Zhang et al.

(10) Patent No.: US 7,662,745 B2
(45) Date of Patent: Feb. 16, 2010

(54) STRETCHABLE ABSORBENT COMPOSITES HAVING HIGH PERMEABILITY

(75) Inventors: Xiaomin Zhang, Appleton, WI (US); Jian Qin, Appleton, WI (US); Lisa Marie Jacobsen, Alpharetta, GA (US); David Martin Jackson, Alpharetta, GA (US)

(73) Assignee: Kimberly-Clark Corporation, Neenah, WI (US)

( * ) Notice: Subject to any disclaimer, the term of this patent is extended or adjusted under 35 U.S.C. 154(b) by 770 days.

(21) Appl. No.: 10/739,385

(22) Filed: Dec. 18, 2003

(65) Prior Publication Data

US 2005/0137085 A1 Jun. 23, 2005

(51) Int. Cl.
*B01J 20/22* (2006.01)
(52) U.S. Cl. ................... 502/401; 502/402
(58) Field of Classification Search .......... 502/401, 502/402
See application file for complete search history.

(56) References Cited

U.S. PATENT DOCUMENTS

| | | | |
|---|---|---|---|
| 3,338,992 A | 8/1967 | Kinney | |
| 3,339,546 A | 9/1967 | Chen | |
| 3,341,394 A | 9/1967 | Kinney | |
| 3,485,706 A | 12/1969 | Evans | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,855,046 A | 12/1974 | Hansen et al. | |
| 3,901,236 A | 8/1975 | Assarsson et al. | |
| 3,966,865 A | 6/1976 | Nishida et al. | |
| 4,055,180 A | 10/1977 | Karami | |
| 4,076,663 A | 2/1978 | Masuda et al. | |
| 4,100,324 A | 7/1978 | Anderson et al. | |
| 4,286,082 A | 8/1981 | Tsubakimoto et al. | |
| 4,327,728 A | 5/1982 | Elias | |
| 4,340,563 A | 7/1982 | Appel et al. | |
| 4,360,021 A | 11/1982 | Stima | |
| 4,369,156 A | 1/1983 | Mathes et al. | |
| 4,392,908 A | 7/1983 | Dehnel | |
| 4,427,737 A | 1/1984 | Cilento et al. | |
| 4,429,001 A | 1/1984 | Kolpin et al. | |
| 4,469,734 A | 9/1984 | Minto et al. | |
| 4,488,928 A | 12/1984 | Ali Khan et al. | |
| 4,530,353 A | 7/1985 | Lauritzen | |
| 4,542,199 A | 9/1985 | Kaminsky et al. | |
| 4,547,420 A | 10/1985 | Krueger et al. | |
| 4,551,191 A | 11/1985 | Kock et al. | |
| 4,587,154 A | 5/1986 | Hotchkiss et al. | |
| 4,588,630 A | 5/1986 | Shimalla | |
| 4,604,313 A | 8/1986 | McFarland et al. | |
| 4,610,678 A | 9/1986 | Weisman et al. | |
| 4,654,038 A | 3/1987 | Sakurai | |
| 4,655,757 A | 4/1987 | McFarland et al. | |
| 4,704,116 A | 11/1987 | Enloe | |
| 4,715,918 A | 12/1987 | Lang | |
| 4,724,114 A | 2/1988 | McFarland et al. | |
| 4,729,371 A | 3/1988 | Krueger et al. | |
| 4,767,825 A | 8/1988 | Pazos et al. | |
| 4,775,579 A | 10/1988 | Hagy et al. | |
| 4,795,668 A | 1/1989 | Krueger et al. | |
| 4,803,117 A | 2/1989 | Daponte | |
| 4,806,408 A | 2/1989 | Pierre et al. | |
| 4,818,464 A | 4/1989 | Lau | |
| 4,834,738 A | 5/1989 | Kielpikowski et al. | |
| RE32,957 E | 6/1989 | Elias | |
| 4,838,885 A | 6/1989 | Bernardin | |
| 4,865,596 A | 9/1989 | Weisman et al. | |
| 4,879,170 A | 11/1989 | Radwanski et al. | |

(Continued)

FOREIGN PATENT DOCUMENTS

DE 29614542 U1 12/1996

(Continued)

OTHER PUBLICATIONS

American Society for Testing Materials (ASTM) Designation: D1238-70, "Standard Method for Measuring Flow Rates of Thermoplastics by Extrusion Plastometer," pp. 415-426, effective Jun. 1970.
"Molecular Weight Distributions," Encyclopedia of Polymer Science and Engineering, Second Edition, vol. 3, John Wiley & Sons, New York, 1985, pp. 299-300.
Coates, Geoffrey W. and Robert M. Waymouth, "Oscillating Stereocontrol: A strategy for the Synthesis of Thermoplastic Elastomeric Polypropylene," Science, vol. 267, Jan. 13, 1995, pp. 217-219.
Cowie, J.M.G., "Solubility and the Cohesive Energy Density," *Polymers: Chemistry and Physics of Modern Materials*, Intext Educational Publishers, New York, 1973, pp. 142-145.

(Continued)

*Primary Examiner*—Edward M Johnson
(74) *Attorney, Agent, or Firm*—Armstrong Teasdale LLP

(57) ABSTRACT

A stretchable absorbent composite having a Composite Permeability of about 10 Darcy or more, or about 15 Darcy or more, and Composite Stretchability of about 30% or more, or about 50% or more, or about 100% or more, and a method of making such a stretchable absorbent composite. The stretchable absorbent composite includes a superabsorbent material, an elastomeric material, and, optionally, pulp fibers. More particularly, the stretchable absorbent composite may include between about 30% and about 85% by weight superabsorbent material, between about 5% and about 25% by weight elastomeric material, and between about 10% and about 70% by weight pulp fibers. The stretchability and liquid handling abilities of the stretchable absorbent composite renders the stretchable absorbent composite suitable for incorporation into a variety of absorbent articles, including personal care products, health/medical absorbent articles, and household/industrial absorbent articles, for example.

31 Claims, 4 Drawing Sheets

U.S. PATENT DOCUMENTS

| | | |
|---|---|---|
| 4,880,419 A | 11/1989 | Ness |
| 4,891,258 A | 1/1990 | Fahrenkrug |
| 4,904,440 A | 2/1990 | Angstadt |
| 4,923,914 A | 5/1990 | Nohr et al. |
| 4,935,022 A | 6/1990 | Lash et al. |
| 4,939,016 A | 7/1990 | Radwanski et al. |
| 4,940,464 A | 7/1990 | Van Gompel et al. |
| 4,957,795 A | 9/1990 | Riedel |
| 4,960,477 A | 10/1990 | Mesek |
| 4,988,344 A | 1/1991 | Reising et al. |
| 4,996,091 A | 2/1991 | McIntyre |
| 5,057,166 A | 10/1991 | Young, Sr. et al. |
| 5,064,689 A | 11/1991 | Young, Sr. et al. |
| 5,064,802 A | 11/1991 | Stevens et al. |
| 5,108,820 A | 4/1992 | Kaneko et al. |
| 5,114,781 A | 5/1992 | Morman |
| 5,116,662 A | 5/1992 | Morman |
| 5,143,680 A | 9/1992 | Molnar et al. |
| 5,149,335 A | 9/1992 | Kellenberger et al. |
| 5,154,715 A | 10/1992 | Van Iten |
| 5,169,706 A | 12/1992 | Collier, IV et al. |
| 5,171,391 A | 12/1992 | Chmielewski et al. |
| 5,188,624 A | 2/1993 | Young, Sr. et al. |
| 5,189,192 A | 2/1993 | LaPointe et al. |
| 5,204,429 A | 4/1993 | Kaminsky et al. |
| 5,213,881 A | 5/1993 | Timmons et al. |
| 5,221,275 A | 6/1993 | Van Iten |
| 5,225,014 A | 7/1993 | Ogata et al. |
| 5,230,959 A | 7/1993 | Young, Sr. et al. |
| 5,248,524 A | 9/1993 | Soderlund |
| 5,260,126 A | 11/1993 | Collier, IV et al. |
| 5,272,236 A | 12/1993 | Lai et al. |
| 5,273,596 A | 12/1993 | Newkirk |
| 5,278,272 A | 1/1994 | Lai et al. |
| 5,279,854 A | 1/1994 | Kendall et al. |
| 5,281,207 A | 1/1994 | Chmielewski et al. |
| 5,281,209 A | 1/1994 | Osborn, III et al. |
| 5,284,703 A | 2/1994 | Everhart et al. |
| 5,288,791 A | 2/1994 | Collier, IV et al. |
| 5,290,626 A | 3/1994 | Nishioi et al. |
| 5,302,447 A | 4/1994 | Ogata et al. |
| 5,308,906 A | 5/1994 | Taylor et al. |
| 5,332,613 A | 7/1994 | Taylor et al. |
| 5,336,552 A | 8/1994 | Strack et al. |
| 5,344,416 A | 9/1994 | Niihara |
| 5,349,100 A | 9/1994 | Mintz |
| 5,350,597 A | 9/1994 | Pelley |
| 5,350,624 A | 9/1994 | Georger et al. |
| 5,352,749 A | 10/1994 | Dechellis et al. |
| 5,354,400 A | 10/1994 | Lavash et al. |
| 5,364,382 A | 11/1994 | Latimer et al. |
| 5,366,793 A | 11/1994 | Fitts, Jr. et al. |
| 5,372,885 A | 12/1994 | Tabor et al. |
| 5,374,696 A | 12/1994 | Rosen et al. |
| 5,376,198 A | 12/1994 | Fahrenkrug et al. |
| 5,382,400 A | 1/1995 | Pike et al. |
| 5,385,775 A | 1/1995 | Wright |
| 5,387,208 A | 2/1995 | Ashton et al. |
| 5,389,094 A | 2/1995 | Lavash et al. |
| 5,389,202 A | 2/1995 | Everhart et al. |
| 5,411,497 A | 5/1995 | Tanzer et al. |
| 5,421,940 A | 6/1995 | Cornils et al. |
| 5,424,115 A | 6/1995 | Stokes |
| 5,425,725 A | 6/1995 | Tanzer et al. |
| 5,432,000 A | 7/1995 | Young, Sr. et al. |
| 5,433,715 A | 7/1995 | Tanzer et al. |
| 5,458,592 A | 10/1995 | Abuto et al. |
| 5,486,166 A | 1/1996 | Bishop et al. |
| 5,490,846 A | 2/1996 | Ellis et al. |
| 5,503,908 A | 4/1996 | Faass |
| 5,508,102 A | 4/1996 | Georger et al. |
| 5,509,914 A | 4/1996 | Osborn, III |
| 5,509,915 A | 4/1996 | Hanson et al. |
| 5,511,960 A | 4/1996 | Terakawa et al. |
| 5,516,585 A | 5/1996 | Young, Sr. et al. |
| 5,518,801 A | 5/1996 | Chappell et al. |
| 5,520,673 A | 5/1996 | Yarbrough et al. |
| 5,527,300 A | 6/1996 | Sauer |
| 5,560,878 A | 10/1996 | Dragoo et al. |
| 5,562,645 A | 10/1996 | Tanzer et al. |
| 5,562,646 A | 10/1996 | Goldman et al. |
| 5,567,472 A | 10/1996 | Siegfried et al. |
| 5,591,147 A | 1/1997 | Couture-Dorschner et al. |
| 5,591,149 A | 1/1997 | Cree et al. |
| 5,593,399 A | 1/1997 | Tanzer et al. |
| 5,599,335 A | 2/1997 | Goldman et al. |
| 5,601,542 A | 2/1997 | Melius et al. |
| 5,611,790 A | 3/1997 | Osborn, III et al. |
| 5,614,283 A | 3/1997 | Potnis et al. |
| 5,620,430 A | 4/1997 | Bamber |
| 5,643,245 A | 7/1997 | Osborn, III et al. |
| 5,645,542 A | 7/1997 | Anjur et al. |
| 5,669,894 A | 9/1997 | Goldman et al. |
| 5,670,044 A | 9/1997 | Ogata et al. |
| 5,676,660 A | 10/1997 | Mukaida et al. |
| 5,679,042 A | 10/1997 | Varona |
| 5,681,305 A | 10/1997 | Korpman |
| 5,683,752 A | 11/1997 | Popp et al. |
| 5,691,035 A | 11/1997 | Chappell et al. |
| 5,704,930 A | 1/1998 | Lavash et al. |
| 5,713,881 A | 2/1998 | Rezai et al. |
| 5,713,884 A | 2/1998 | Osborn, III et al. |
| 5,713,885 A | 2/1998 | Jorgenson et al. |
| 5,718,913 A | 2/1998 | Dhuique-Mayer et al. |
| 5,720,832 A | 2/1998 | Minto et al. |
| 5,759,926 A | 6/1998 | Pike et al. |
| 5,766,389 A | 6/1998 | Brandon et al. |
| 5,772,648 A | 6/1998 | Osborn, III et al. |
| 5,789,065 A | 8/1998 | Haffner et al. |
| 5,820,973 A | 10/1998 | Dodge, II et al. |
| 5,824,004 A | 10/1998 | Osborn, III et al. |
| 5,833,678 A | 11/1998 | Ashton et al. |
| 5,843,059 A | 12/1998 | Niemeyer et al. |
| 5,849,000 A | 12/1998 | Anjur et al. |
| 5,853,881 A | 12/1998 | Estey et al. |
| 5,858,292 A | 1/1999 | Dragoo et al. |
| 5,858,515 A | 1/1999 | Stokes et al. |
| 5,879,751 A | 3/1999 | Bogdanski |
| 5,882,769 A | 3/1999 | McCormack et al. |
| 5,883,028 A | 3/1999 | Morman et al. |
| 5,891,120 A | 4/1999 | Chmielewski |
| 5,900,109 A | 5/1999 | Sanders et al. |
| 5,904,675 A | 5/1999 | Laux et al. |
| 5,922,163 A | 7/1999 | Helynranta et al. |
| 5,938,650 A | 8/1999 | Baer et al. |
| 5,964,743 A | 10/1999 | Abuto et al. |
| 5,977,014 A | 11/1999 | Plischke et al. |
| 5,981,410 A | 11/1999 | Hansen et al. |
| 5,981,689 A | 11/1999 | Mitchell et al. |
| 5,994,440 A | 11/1999 | Staples et al. |
| 6,013,062 A | 1/2000 | Dilnik |
| 6,046,377 A | 4/2000 | Huntoon et al. |
| 6,060,115 A | 5/2000 | Borowski et al. |
| 6,068,620 A | 5/2000 | Chmielewski |
| 6,072,101 A | 6/2000 | Beihoffer et al. |
| 6,080,909 A | 6/2000 | Osterdahl et al. |
| 6,087,448 A | 7/2000 | Mitchell et al. |
| 6,090,875 A | 7/2000 | Staples et al. |
| 6,102,902 A | 8/2000 | Jackson |
| 6,121,409 A | 9/2000 | Mitchell et al. |
| 6,129,720 A | 10/2000 | Blenke et al. |
| 6,159,591 A | 12/2000 | Beihoffer et al. |
| 6,194,631 B1 | 2/2001 | Mitchell et al. |
| 6,200,297 B1 | 3/2001 | Boulanger |

| | | |
|---|---|---|
| 6,214,274 B1 | 4/2001 | Melius et al. |
| 6,221,062 B1 | 4/2001 | Osborn, III |
| 6,222,091 B1 | 4/2001 | Beihoffer et al. |
| 6,231,557 B1 | 5/2001 | Krautkramer et al. |
| 6,235,965 B1 | 5/2001 | Beihoffer et al. |
| 6,241,713 B1 | 6/2001 | Gross et al. |
| 6,248,202 B1 | 6/2001 | Corzani et al. |
| 6,261,679 B1 | 7/2001 | Chen et al. |
| 6,264,784 B1 | 7/2001 | Menard et al. |
| 6,277,105 B1 | 8/2001 | Rynish |
| 6,280,428 B1 | 8/2001 | Lash et al. |
| 6,287,288 B1 | 9/2001 | Osborn, III et al. |
| 6,290,686 B1 | 9/2001 | Tanzer |
| 6,309,378 B1 | 10/2001 | Costa |
| 6,312,416 B1 | 11/2001 | Brisebois et al. |
| 6,328,722 B1 | 12/2001 | Lavash et al. |
| 6,342,298 B1 | 1/2002 | Evans et al. |
| 6,353,148 B1 | 3/2002 | Gross |
| 6,362,389 B1 | 3/2002 | McDowall et al. |
| 6,371,950 B1 | 4/2002 | Roslansky et al. |
| 6,372,952 B1 | 4/2002 | Lash et al. |
| 6,376,072 B1 | 4/2002 | Evans et al. |
| 6,387,495 B1 | 5/2002 | Reeves et al. |
| 6,392,116 B1 | 5/2002 | Beihoffer et al. |
| 6,403,857 B1 | 6/2002 | Gross et al. |
| 6,416,502 B1 | 7/2002 | Connelly et al. |
| 6,428,523 B1 | 8/2002 | Proglhof |
| 6,429,350 B1 | 8/2002 | Tanzer et al. |
| 6,440,113 B1 | 8/2002 | Brisebois et al. |
| 6,441,266 B1 | 8/2002 | Dyer et al. |
| 6,455,114 B1 | 9/2002 | Goldhirsch et al. |
| 6,455,753 B1 | 9/2002 | Glaug et al. |
| 6,465,712 B1 * | 10/2002 | Matthews et al. ............ 604/378 |
| 6,468,942 B1 * | 10/2002 | Sansalone ................... 502/402 |
| 6,470,943 B1 | 10/2002 | Borowski et al. |
| 6,494,871 B1 | 12/2002 | Lariviere et al. |
| 6,500,159 B1 | 12/2002 | Carvalho |
| 6,503,234 B1 | 1/2003 | Canuel et al. |
| 6,509,512 B1 | 1/2003 | Beihoffer et al. |
| 6,509,513 B2 | 1/2003 | Glaug et al. |
| 6,515,195 B1 | 2/2003 | Lariviere et al. |
| 6,527,757 B1 | 3/2003 | Jackson |
| 6,534,572 B1 | 3/2003 | Ahmed et al. |
| 6,552,245 B1 | 4/2003 | Roessler et al. |
| 6,555,502 B1 | 4/2003 | Beihoffer et al. |
| 6,562,742 B2 | 5/2003 | Dutkiewicz et al. |
| 6,570,058 B1 | 5/2003 | Fuchs et al. |
| 6,579,274 B1 | 6/2003 | Morman et al. |
| 6,582,413 B2 | 6/2003 | Krautkramer et al. |
| 6,590,138 B2 | 7/2003 | Onishi |
| 6,603,054 B2 | 8/2003 | Chen et al. |
| 6,605,552 B2 | 8/2003 | Jackson et al. |
| 6,610,900 B1 | 8/2003 | Tanzer |
| 6,627,564 B1 | 9/2003 | Morman et al. |
| 6,632,209 B1 | 10/2003 | Chmielewski |
| 6,641,134 B1 | 11/2003 | Dobbertin et al. |
| 6,641,695 B2 | 11/2003 | Baker |
| 6,645,190 B1 | 11/2003 | Olson et al. |
| 6,646,179 B1 | 11/2003 | Melius et al. |
| 6,646,180 B1 | 11/2003 | Chmielewski |
| 6,680,423 B1 | 1/2004 | Tanzer |
| 2001/0001312 A1 | 5/2001 | Mitchell et al. |
| 2001/0007064 A1 | 7/2001 | Mitchell et al. |
| 2001/0029358 A1 | 10/2001 | Beihoffer et al. |
| 2001/0044612 A1 | 11/2001 | Beihoffer et al. |
| 2002/0007166 A1 | 1/2002 | Mitchell et al. |
| 2002/0015846 A1 | 2/2002 | Evans et al. |
| 2002/0077618 A1 | 6/2002 | Molas |
| 2002/0095127 A1 | 7/2002 | Fish et al. |
| 2002/0150761 A1 | 10/2002 | Lange et al. |
| 2002/0156441 A1 | 10/2002 | Sawyer et al. |
| 2002/0183703 A1 | 12/2002 | Singh et al. |
| 2003/0014027 A1 | 1/2003 | Beihoffer et al. |
| 2003/0060112 A1 | 3/2003 | Rezai et al. |
| 2003/0105441 A1 | 6/2003 | Chmielewski |
| 2003/0114071 A1 | 6/2003 | Everhart et al. |
| 2003/0116888 A1 | 6/2003 | Rymer et al. |
| 2003/0118764 A1 | 6/2003 | Adams et al. |
| 2003/0129915 A1 | 7/2003 | Harriz |
| 2003/0134102 A1 | 7/2003 | Wang et al. |
| 2003/0158531 A1 | 8/2003 | Chmielewski |
| 2003/0171729 A1 | 9/2003 | Kaun et al. |
| 2004/0019168 A1 | 1/2004 | Soerens et al. |
| 2004/0054341 A1 | 3/2004 | Kellenberger et al. |
| 2004/0054342 A1 | 3/2004 | Newbill et al. |
| 2004/0116014 A1 | 6/2004 | Soerens et al. |
| 2004/0116287 A1 | 6/2004 | Wang et al. |
| 2004/0158212 A1 | 8/2004 | Ponomarenko et al. |
| 2004/0203308 A1 | 10/2004 | Ko et al. |
| 2004/0222568 A1 | 11/2004 | Armantrout et al. |
| 2005/0027268 A1 | 2/2005 | Qin et al. |
| 2005/0096435 A1 | 5/2005 | Smith et al. |
| 2005/0096623 A1 | 5/2005 | Nhan et al. |
| 2005/0101929 A1 | 5/2005 | Waksmundzki et al. |
| 2005/0107759 A1 | 5/2005 | Waksmundzki et al. |
| 2005/0124959 A1 | 6/2005 | Alcantara et al. |
| 2005/0137085 A1 | 6/2005 | Zhang et al. |
| 2005/0186351 A1 | 8/2005 | Fung et al. |
| 2005/0228350 A1 | 10/2005 | Ranganathan et al. |
| 2006/0004336 A1 | 1/2006 | Zhang et al. |
| 2006/0005919 A1 | 1/2006 | Schewe et al. |
| 2006/0069365 A1 | 3/2006 | Sperl et al. |
| 2006/0127688 A1 | 6/2006 | Busch et al. |
| 2006/0135932 A1 | 6/2006 | Abuto et al. |

FOREIGN PATENT DOCUMENTS

| | | |
|---|---|---|
| EP | 0270058 A1 | 6/1988 |
| EP | 0 315 507 B1 | 5/1989 |
| EP | 0324097 B1 | 7/1989 |
| EP | 0 333 209 B1 | 9/1989 |
| EP | 0 341 870 A2 | 11/1989 |
| EP | 0 179 937 B1 | 4/1990 |
| EP | 0471114 B1 | 2/1992 |
| EP | 0 492 554 B1 | 7/1992 |
| EP | 0 497 072 A1 | 8/1992 |
| EP | 0 534 863 A1 | 3/1993 |
| EP | 0548714 B1 | 6/1993 |
| EP | 0572033 B1 | 12/1993 |
| EP | 0598413 A1 | 5/1994 |
| EP | 0 601 610 A1 | 6/1994 |
| EP | 0 633 009 A2 | 1/1995 |
| EP | 0 700 672 A1 | 3/1996 |
| EP | 0 700 673 A1 | 3/1996 |
| EP | 0779065 B1 | 6/1997 |
| EP | 0 788 336 B1 | 8/1997 |
| EP | 0 788 874 B1 | 8/1997 |
| EP | 0 794 751 B2 | 9/1997 |
| EP | 0 794 751 B2 | 6/1999 |
| EP | 0 788 874 B1 | 9/1999 |
| EP | 0 947 549 A1 | 10/1999 |
| EP | 0957870 B1 | 11/1999 |
| EP | 0967950 B1 | 1/2000 |
| EP | 0 788 336 B1 | 6/2000 |
| EP | 1 013 291 A1 | 6/2000 |
| EP | 1077052 A1 | 2/2001 |
| EP | 1077053 A2 | 2/2001 |
| EP | 1078616 A2 | 2/2001 |
| EP | 1161928 B1 | 12/2001 |
| EP | 1245209 A2 | 10/2002 |
| EP | 0 994 686 B1 | 11/2002 |
| EP | 1285643 A2 | 2/2003 |
| EP | 0 802 949 B1 | 5/2003 |
| GB | 2 151 272 A | 7/1985 |
| GB | 2273659 A | 6/1994 |
| JP | 04-065568 A | 3/1992 |

| | | | |
|---|---|---|---|
| JP | 07-138866 A | 5/1995 | |
| JP | 07163620 A | 6/1995 | |
| WO | WO 93/15249 A1 | 8/1993 | |
| WO | WO 95/10995 | 4/1995 | |
| WO | 9520931 A1 | 8/1995 | |
| WO | WO 96/11107 A1 | 4/1996 | |
| WO | WO 96/14885 | 5/1996 | |
| WO | WO 96/16624 A2 | 6/1996 | |
| WO | 9707761 A1 | 3/1997 | |
| WO | WO 97/39780 A1 | 10/1997 | |
| WO | WO 98/03710 A1 | 1/1998 | |
| WO | WO 98/45519 A1 | 10/1998 | |
| WO | WO 99/00093 | 1/1999 | |
| WO | WO 99/00095 | 1/1999 | |
| WO | WO 99/25393 A2 | 5/1999 | |
| WO | WO 99/25745 A1 | 5/1999 | |
| WO | WO 99/25748 A1 | 5/1999 | |
| WO | 0009058 A1 | 2/2000 | |
| WO | 0037735 A1 | 6/2000 | |
| WO | WO 00/37000 | 6/2000 | |
| WO | WO 00/37009 A2 | 6/2000 | |
| WO | WO 00/37735 | 6/2000 | |
| WO | WO 00/56959 A1 | 9/2000 | |
| WO | 0059438 A1 | 10/2000 | |
| WO | WO 00/59439 A1 | 10/2000 | |
| WO | WO 00/63295 A1 | 10/2000 | |
| WO | WO 01/15650 A1 | 3/2001 | |
| WO | 0147456 A1 | 7/2001 | |
| WO | WO 02/10032 A2 | 2/2002 | |
| WO | WO 02/24132 A2 | 3/2002 | |
| WO | WO 02/34184 A1 | 5/2002 | |
| WO | WO 02/43784 A2 | 6/2002 | |
| WO | WO 02/053378 A2 | 7/2002 | |
| WO | 03015560 A1 | 2/2003 | |
| WO | 03015682 A1 | 2/2003 | |
| WO | 03015684 A1 | 2/2003 | |
| WO | WO 03/018671 A1 | 3/2003 | |
| WO | WO 03/037392 A1 | 5/2003 | |
| WO | WO 03/047485 A1 | 6/2003 | |
| WO | WO 03/051411 A1 | 6/2003 | |
| WO | WO 03/051417 A1 | 6/2003 | |
| WO | WO 03/053297 A2 | 7/2003 | |
| WO | WO 03/053319 A2 | 7/2003 | |
| WO | WO 03/057268 A1 | 7/2003 | |
| WO | WO 03/057964 A1 | 7/2003 | |
| WO | WO 03/068122 A1 | 8/2003 | |
| WO | 03099186 A1 | 12/2003 | |
| WO | 2004084784 A1 | 10/2004 | |
| WO | WO 2005/044163 A1 | 5/2005 | |
| WO | 2007070776 A2 | 6/2007 | |

OTHER PUBLICATIONS

Lawrence, K.D. et al., "An Improved Device For the Formation of Superfine, Thermoplastic Fibers," *NRL Report 5265*, U.S. Naval Research Laboratory, Washington, D.C., Feb. 11, 1959, pp. 1-7.

Neumann, A.W., and R.J. Good, "Techniques of Measuring Contact Angles," Chapter 2, *Surface and Colloid Science—Experimental Methods*, vol. 11, edited by R.J. Good and R.R. Stromberg, Plenum Press, 1979, pp. 31-91.

Wagener, K.B., "Oscillating Catalysts: A New Twist for Plastics," *Science*, vol. 267, Jan. 13, 1995, p. 191.

Wente, V.A. et al., "Manufacture of Superfine Organic Fibers," *NRL Report 4364*, U.S. Naval Research Laboratory, Washington, D.C., May 25, 1954, pp. 1-15.

"Normal Distribution," graph, partial citation from Wikipedia entry; full entry annotated with citations and bibliography, "http://en.wikipedia.org/wiki/Normal_distribution", 1 page.

ASTM D 737-96.

ASTM F 316-03.

ASTM D 5035-90.

Fed.Test Meth.STD. 191A-Meth 5450.

Non-final Office Action issued in U.S. Appl. No. 10/883,174 mailed Jan. 26, 2009.

Non-final Office Action issued in U.S. Appl. No. 10/883,174 mailed Mar. 21, 2009.

\* cited by examiner

STRETCHABLE ABSORBENT COMPOSITES HAVING HIGH PERMEABILITY

BACKGROUND OF THE INVENTION

Absorbent composites are incorporated into a variety of absorbent articles, including personal care products, health/medical products, and household/industrial products, for example. Conventional absorbent composites are typically not stretchable.

Elastomeric materials have been incorporated into various structural components of absorbent articles to achieve a better fit, greater comfort, and enhanced containment. For example, absorbent articles having stretchable outer covers and/or stretchable body side liners are disclosed in U.S. Pat. No. 4,834,738 issued to Kielpikowski, et al. and in PCT Publication No. WO 02/34184 in the name of Vukos, et al. Adding stretchability to absorbent composites is difficult because elastomeric materials per se are not absorbent, and the addition of elastomeric materials to absorbent composites typically inhibits the liquid handling properties of the absorbent composites. More particularly, the relatively large resistant force or retraction force of elastic matrices leads to low liquid intake rates/permeability due to significant reduction of inter-particle void volume, and the low wettability of elastomeric materials results in poor liquid distribution.

A number of stretchable absorbent composite materials have been developed, such as described in U.S. Pat. No. 6,362,389 issued to McDowall et al. However, existing stretchable absorbent composites have not been optimized to achieve an optimum range of liquid handling abilities. Low liquid intake rates, or low liquid permeability, causes high-speed, high-pressure, liquid insults to either pool on top of or run off the sides of the absorbent composite before the absorbent composite has a chance to absorb all of the liquid. Furthermore, in the absence of suitable liquid distribution capabilities, liquid insults cannot be sufficiently directed to unsaturated areas of the absorbent composite when necessary.

There is a need or desire for absorbent composites that are stretchable and have sufficient composite permeability. There is a further need or desire for an absorbent article including a stretchable absorbent composite with optimum liquid handling abilities. There is yet a further need or desire for a method of making a stretchable absorbent composite having optimum liquid handling abilities.

SUMMARY OF THE INVENTION

It has been discovered that a combination of high stretchability and permeability in an absorbent composite provides both fit and fluid management capabilities in absorbent articles. Thus, the present invention is directed to absorbent composites having a Composite Permeability of about 15 Darcy ($10^{-8}$ cm$^2$) or greater, and a Composite Stretchability of about 50% or more.

Another embodiment of the invention is directed to absorbent composites including about 60 weight percent or more of superabsorbent while having a Composite Permeability of about 15 Darcy or greater, and a Composite Stretchability of about 30% or more.

Yet another embodiment of the invention is directed to absorbent composites having a Composite Permeability of about 10 Darcy or greater, and a Composite Stretchability of about 100% or more.

To achieve the absorbent composites of the invention, suitable superabsorbent materials, elastomeric materials, and, optionally, pulp fibers are selected and combined in optimum ratios. More particularly, the absorbent composites may include between about 5% and about 95%, or between about 50% and about 95%, or between about 30% and about 85% by weight superabsorbent material; between about 5% and about 25%, or between about 8% and about 18% by weight elastomeric material; and between about 0% and about 75%, or between about 10% and about 70% by weight pulp fibers.

The Composite Permeability of the absorbent composites is dependent, at least in part, on the properties of the superabsorbent material. The superabsorbent material used in the absorbent composites should have sufficient absorbent capacity and gel strength force to open up the structure of the stretchable matrix within the absorbent composite, especially under pressure. Thus, the superabsorbent material suitably has a gel bed permeability (GBP) under 0.3 psi pressure of about 30 Darcy or greater. In general, the lower the amount of superabsorbent material and/or elastomeric material in the absorbent composite, the lower the gel bed permeability under 0.3 psi pressure requirement is for the superabsorbent material. In certain embodiments, the superabsorbent material may be in the form of pre-screened 300-600 micron particles. Additionally, in various embodiments, the superabsorbent material may be surface-treated with a polyvinyl amine solution.

Examples of suitable elastomeric materials include elastomeric polymer compositions, which may include olefinic copolymers, polyethylene elastomers, polypropylene elastomers, polyester elastomers, ethylene-propylene-diene terpolymers, styrene-isoprene-styrene, styrene-butadiene-styrene, styrene-ethylene/butylene-styrene, styrene-ethylene/propylene-styrene, polyurethane, polyisoprene, cross-linked polybutadiene, or a combination of any of these polymeric materials.

The stretchable absorbent composites are suitable for use in a variety of absorbent articles including, but not limited to, personal care products, health/medical absorbent articles, household/industrial absorbent articles, and the like. In particular, the absorbent composite may be positioned between an outer cover and a body side liner in an absorbent article, and the outer cover and/or the body side liner may be elastomeric or at least stretchable.

One method of making the stretchable absorbent composites includes extruding an elastomeric material through at least one meltblown die, fiberizing a plurality of pulp fibers, and mixing superabsorbent material with the fiberized pulp fibers and the extruded elastomeric material. An aqueous surfactant mixture can be sprayed onto the mixture of superabsorbent material, fiberized pulp fibers, and extruded elastomeric material while transferring the mixture of superabsorbent material, fiberized pulp fibers, and extruded elastomeric material onto a conveyor.

With the foregoing in mind, it is a feature and advantage of the invention to provide absorbent composites that are stretchable and have sufficient Composite Permeability, as well as methods of making such absorbent composites, and absorbent articles including such absorbent composites.

BRIEF DESCRIPTION OF THE DRAWINGS

These and other objects and features of this invention will be better understood from the following detailed description taken in conjunction with the drawings, wherein.

DEFINITIONS

Figure 1:
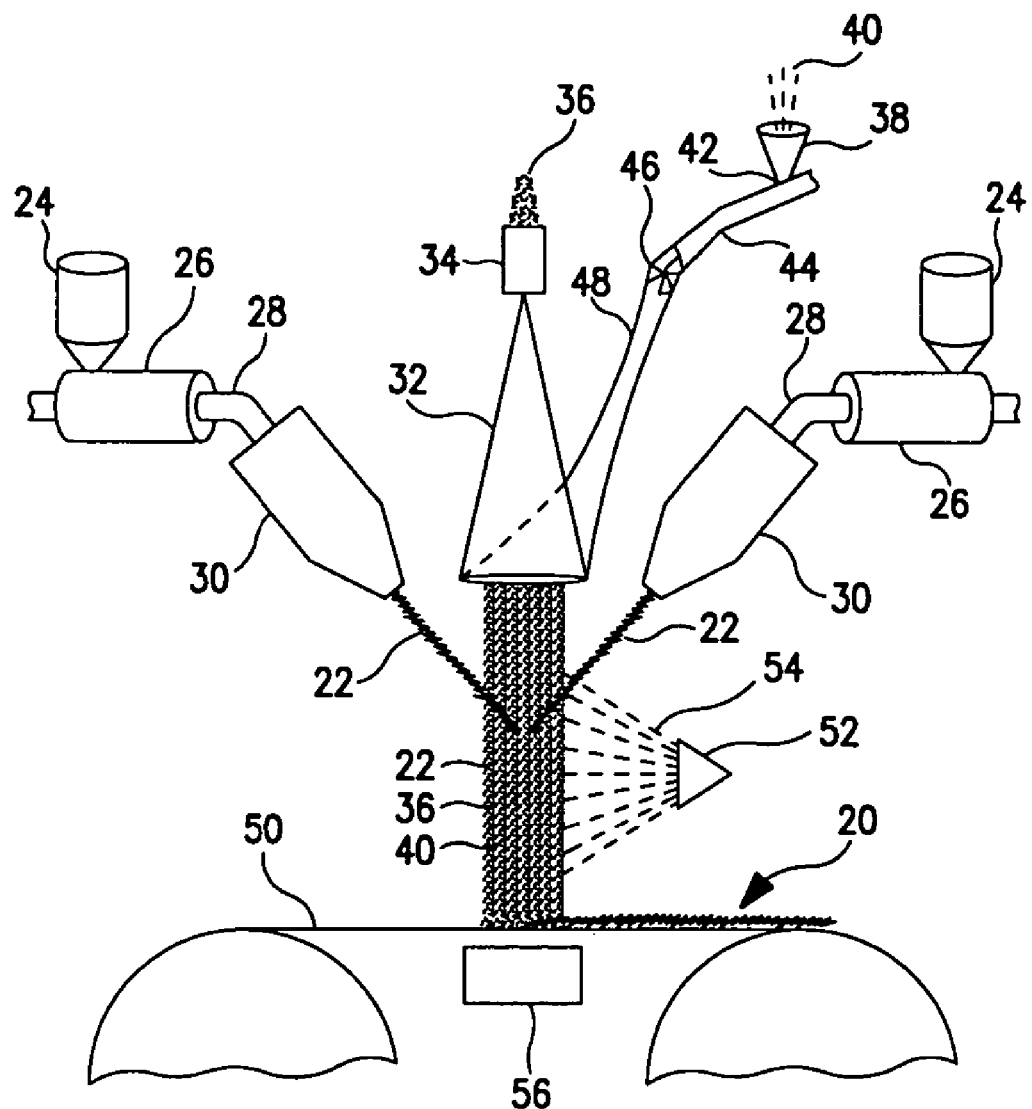
FIG. 1 shows a schematic diagram of one version of a method and apparatus for producing an absorbent composite.

Within the context of this specification, each term or phrase below will include the following meaning or meanings.

"Elastomeric" and "elastic" are used interchangeably to refer to a material or composite that is generally capable of recovering its shape after deformation when the deforming force is removed. Specifically, as used herein, elastic or elastomeric is meant to be that property of any material which, upon application of a biasing force, permits the material to be stretchable to a stretched biased length which is at least about 50 percent greater than its relaxed unbiased length, and that will cause the material to recover at least 40 percent of its elongation upon release of the stretching force. A hypothetical example which would satisfy this definition of an elastomeric material would be a one (1) inch sample of a material which is elongatable to at least 1.50 inches and which, upon being elongated to 1.50 inches and released, will recover to a length of less than 1.30 inches. Many elastic materials may be stretched by much more than 50 percent of their relaxed length, and many of these will recover to substantially their original relaxed length upon release of the stretching force.

"Layer" when used in the singular can have the dual meaning of a single element or a plurality of elements.

"Liquid-impermeable" when used to describe a layer or laminate means that liquid such as water or bodily fluids will not pass through the layer or laminate under ordinary use conditions in a direction generally perpendicular to the plane of the layer or laminate at the point of liquid contact.

"Liquid-permeable" refers to a layer or laminate that is not liquid-impermeable.

"Meltblown fiber" refers to fibers formed by extruding a molten thermoplastic material through a plurality of fine, usually circular or rectangular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally equal to or smaller than about 6 denier, and are generally self-bonding and also bond with other non-molten components when deposited onto a collecting surface.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible configurational isomers of the material. These configurations include, but are not limited to isotactic, syndiotactic and atactic symmetries.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein by reference in its entirety in a manner consistent with the present document. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, by at least 30% (to at least 130% of its initial (unstretched) length) in at least one direction, suitably by at least 50% (to at least 150% of its initial length), or by at least 100% (to at least 200% of its initial length). The term includes elastic materials that are both extensible and retractable, as well as materials that stretch but do not significantly retract. A hypothetical example which would satisfy this definition of an extensible material would be a one (1) inch sample of a material which is elongatable by at least 30% to at least 1.30 inches.

"Superabsorbent" refers to a water-swellable, water-insoluble organic or inorganic material capable, under the most favorable conditions, of absorbing at least about 10 times its weight, or at least about 15 times its weight, or at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. The superabsorbent material may be biodegradable or non-biodegradable. The superabsorbent materials can include particles, fibers, tows, flakes, films, foams, and the like. A material is "absorbent" if it absorbs at least five times its weight of the aqueous solution under these conditions.

"Absorbent article" includes, but is not limited to, personal care absorbent articles, health/medical absorbent articles, and household/industrial absorbent articles.

"Personal care absorbent article" includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads, containers, incontinence products, and urinary shields; clothing components; bibs; athletic and recreation products; and the like.

"Health/medical absorbent article" includes a variety of professional and consumer health-care products including, but not limited to, products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads, and the like.

"Household/industrial absorbent articles" include construction and packaging supplies, products for cleaning and disinfecting, wipes, covers, filters, towels, disposable cutting sheets, bath tissue, facial tissue, nonwoven roll goods, home-comfort products including pillows, pads, cushions, masks and body care products such as products used to cleanse or treat the skin, laboratory coats, cover-alls, trash bags, stain removers, topical compositions, laundry soil/ink absorbers, detergent agglomerators, lipophilic fluid separators, and the like.

These terms may be defined with additional language in the remaining portions of the specification.

DESCRIPTION OF PREFERRED EMBODIMENTS

In accordance with the invention, stretchable absorbent composites having high permeability are provided for use in a variety of articles. A method of making these stretchable absorbent composites is also provided.

Stretchability and liquid permeability are two properties that, when present in absorbent composites, are inversely proportionate. It is difficult to provide both of these properties at sufficient levels in absorbent composites. The absorbent composites of the invention are designed to have sufficient stretchability as well as sufficient permeability through a combination of carefully selected superabsorbent materials, elastomeric materials, and pulp fibers in balanced ratios.

As a result, the absorbent composites have a Composite Stretchability of about 30% or more, or about 50% or more, or about 100% or more. Stretchability of any stretchable material is a function of both material/structure aspects and testing conditions. Therefore, the levels of stretchability referred to herein are used in reference to determinations based on the Stretchability Testing procedure provided in the Test Methods section below.

The Composite Stretchability of the absorbent composites renders the absorbent composites particularly suitable for use in combination with other stretchable structural components. Stretchability of an absorbent composite depends on the type of elastomeric material in the absorbent composite, as well as the percentage of elastomeric material relative to the other materials included in the absorbent composite. In general, as the percentage of elastomeric material increases, stretchability of the absorbent composite increases. Conversely, with less elastomeric material, the stretchability of the absorbent composite is lower. The effects of elastomeric material on stretchability are illustrated in the Examples below. Absorbent composite structure also affects overall stretchability of the absorbent composites. For example, when a fixed amount of elastomeric material is used in an absorbent composite, an absorbent composite having a more uniform mixing (or dispersion) between elastomeric material and other components will result in a higher stretchability than the one having a less uniform mixing. Other structural factors include fiber size and length of elastomeric material, number of bonds formed and binding strength, basis weight and density of absorbent composites, existence of defects, and the like.

Suitably, the absorbent composite includes between about 5% and about 25% by weight elastomeric material, or between about 8% and about 18% by weight elastomeric material. The elastomeric material may include olefinic copolymers, polyethylene elastomers, polypropylene elastomers, polyester elastomers, polyisoprene, cross-linked polybutadiene, diblock, triblock, tetrablock, or other multi-block thermoplastic elastomeric and/or flexible copolymers such as block copolymers including hydrogenated butadiene-isoprene-butadiene block copolymers; stereoblock polypropylenes; graft copolymers, including ethylene-propylene-diene terpolymer or ethylene-propylene-diene monomer (EPDM), ethylene-propylene random copolymers (EPM), ethylene propylene rubbers (EPR), ethylene vinyl acetate (EVA), and ethylene-methyl acrylate (EMA); and styrenic block copolymers including diblock and triblock copolymers such as styrene-isoprene-styrene (SIS), styrene-butadiene-styrene (SBS), styrene-isoprene-butadiene-styrene (SEBS), styrene-ethylene/butylene-styrene (SEBS), or styrene-ethylene/propylene-styrene (SEPS), which may be obtained from Kraton Inc. of Houston, Tex., under the trade designation KRATON® elastomeric resin or from Dexco, a division of Exxon-Mobil, under the trade designation VECTOR® (SIS and SBS polymers); blends of thermoplastic elastomers with dynamic vulcanized elastomer-thermoplastic blends; thermoplastic polyether ester elastomers; ionomeric thermoplastic elastomers; thermoplastic elastic polyurethanes, including those available from E. I. Du Pont de Nemours Co., under the trade name LYCRA® polyurethane, and ESTANE® available from Noveon, Inc.; thermoplastic elastic polyamides, including polyether block amides available from A to Chemical Company, under the trade name PEBAX® polyether block amide; thermoplastic elastic polyesters, including those available from E. I. Du Pont de Nemours Co., under the trade name HYTREL®, and ARNITEL® from DSM Engineering Plastics of Evansville, Ind., and single-site or metallocene-catalyzed polyolefins having a density of less than about 0.89 grams/cubic centimeter, available from Dow Chemical Co. under the trade name AFFINITY™; and combinations thereof.

As used herein, a tri-block copolymer has an ABA structure where the A represents several repeat units of type A, and B represents several repeat units of type B. As mentioned above, several examples of styrenic block copolymers are SBS, SIS, SIBS, SEBS, and SEPS. In these copolymers the A blocks are polystyrene and the B blocks are a rubbery component. Generally these triblock copolymers have molecular weights that can vary from the low thousands to hundreds of thousands and the styrene content can range from 5% to 75% based on the weight of the triblock copolymer. A diblock copolymer is similar to the triblock but is of an AB structure. Suitable diblocks include styrene-isoprene diblocks, which have a molecular weight of approximately one-half of the triblock molecular weight having the same ratio of A blocks to B blocks.

Composite Permeability is one measure of fluid handling capabilities of an absorbent composite, and can be measured using the test method described in detail below. The absorbent composites of the invention suitably have a Composite Permeability of about 10 Darcy ($10^{-8}$ cm$^2$) or greater, or about 15 Darcy or greater, or about 20 Darcy or greater.

The Composite Permeability of the absorbent composite depends largely on the type of superabsorbent material in the absorbent composite, as well as the percentage of superabsorbent material relative to the other materials included in the absorbent composite. Superabsorbent materials may vary by composition as well as by particle size. For example, one effective approach to achieving higher Composite Permeability is to select a superabsorbent material having a suitable composition with a relatively high GBP under 0.3 psi swell pressure value. Another effective approach is to alter the elastomeric material to create smaller fiber diameters, such as by increasing the primary air on the dies during the composite-forming process, described in greater detail below. In one embodiment, for example, the superabsorbent material may include pre-screened 300-600 micron particles. Yet another effective approach is to decrease the tensile strength of the stretchable matrix within the absorbent composite, such as by reducing the amount of elastomeric material in the absorbent composite.

More particularly, the superabsorbent material should have sufficient absorbent capacity and gel strength to overcome the resistant force of the stretchable matrix within the absorbent composite and to open up the structure of the stretchable matrix, especially when the absorbent composite is under pressure. Gel Bed Permeability (GBP) under 0.3 psi pressure is used herein to assess this requirement for the superabsorbent material. Permeability of the absorbent composite is a function of both the GBP under 0.3 psi pressure and percentage superabsorbent material in the absorbent composite. The superabsorbent material included in the absorbent composite of the invention suitably has a GBP under 0.3 psi pressure of about 30 Darcy or greater, or about 35 Darcy or greater. Most current conventional superabsorbent materials have a GBP under 0.3 psi pressure of about 15 Darcy or lower when they have an ability to absorb at least 20 times their weight in an aqueous solution containing 0.9 weight percent sodium chloride. The superabsorbent material included in the absorbent composites of the invention suitably has a centrifuge retention capacity (CRC) of about 20 grams/gram or more, as determined by the CRC Test Method described in detail below. The absorbent composite suitably includes between about 5% and about 95%, or between about 50% and about 95%, or between about 30% and about 85% by weight superabsorbent material.

As illustrated in the Examples below, superabsorbent material with higher GBP under 0.3 psi pressure is helpful in improving Composite Permeability. For example, in an absorbent composite including about 75% by weight superabsorbent material, the GBP value under 0.3 psi pressure for 300 to 600 micron superabsorbent material is suitably about 30 Darcy or greater. In general, the lower the amount of superabsorbent material in the absorbent composite, the lower the GBP value under 0.3 psi pressure of the superabsorbent material may be required.

The superabsorbent materials can include particulates, fibers, films, foams, non-ionic superabsorbents, and/or polyacrylate superabsorbents, for example. The superabsorbent materials can be selected from natural, synthetic, and modified natural polymers and materials. The superabsorbent materials can be inorganic materials, such as silica gels, or organic compounds, such as crosslinked polymers. Conventional superabsorbent materials are crosslinked polyelectrolytes. Polyelectrolytes include either anionic or cationic polymers. Anionic polymers contain functional groups such as carboxyl, sulfonate, sulphate, sulfite, phosphate, or a mixture thereof. Examples of anionic polymers include, but are not limited to, salts or partial salts of polyacrylic acid, polyacrylamido methylpropane sulfonic acid, polyvinyl acetic acid, polyvinyl phosphonic acid, polyvinyl sulfonic acid, isobutylene-maleic anhydride copolymer, carboxymethyl cellulose, alginic acid, carrageenan, polyaspartic acid, polyglutamic acid, and copolymers or mixtures thereof. Cationic polymers contain functional groups such as primary, secondary, and tertiary amine, imine, amide, quaternary ammonium, or mixtures thereof. Examples of cationic polymers include, but are not limited to, salts or partial salts of polyvinyl amine, polydiallyl dimethyl ammonium hydroxide, polyacrylamidopropyl trimethyl ammonium hydroxide, polyamino propanol vinyl ether, polyallylamine, chitosan, polylysine, polyglutamine, and copolymers or mixtures thereof. Examples of commercially available superabsorbent materials include SXM 9394, SXM 9543, and FAVOR 880, each available from Degussa Superabsorber in Greensboro, N.C., U.S.A., and Dow DRYTECH 2035HP, available from Dow Chemical Co. in Midland, Mich., U.S.A. These and other superabsorbent materials, including surface-treated commercially-available superabsorbents and biodegradable superabsorbents, are suitable for use in the absorbent composites.

Surface-treated superabsorbents generally include a superabsorbent and a surface treatment applied to the outer surface of the superabsorbent. In one particular embodiment, the superabsorbent comprises a cross-linked polymer including about 75 weight percent or more anionic polymer. The term "polymer," as used herein, refers to either a single polymer or to a mixture of polymers. The term "anionic polymer," as used herein, refers to a polymer or mixture of polymers including a functional group or groups having a potential for becoming negatively charged ions upon ionization in an aqueous solution. In certain embodiments, the superabsorbent includes a cross-linked polymer including about 85 weight percent or more anionic polymer, or about 90 weight percent or more anionic polymer. In another embodiment, the superabsorbent includes a cross-linked polymer including about 75 weight percent or more cationic polymer. The term "cationic polymer," as used herein, refers to a polymer or mixture of polymers including a functional group or groups having a potential for becoming positively charged ions upon ionization in an aqueous solution. In certain embodiments, the superabsorbent includes a cross-linked polymer including about 85 weight percent or more cationic polymer, or about 90 weight percent or more cationic polymer.

The surface treatment of the surface-treated superabsorbent includes, at least in part, a water-soluble, non-cross-linked polymer having a potential for becoming charged opposite that of the superabsorbent, applied to all or part of the outer surface of the superabsorbent. For example, where the superabsorbent includes a cross-linked polymer that is generally anionic (e.g., includes about 75% or more by weight anionic polymer), so as to have a potential for becoming negatively charged, the surface treatment, at least in part, includes a water-soluble, non-cross-linked polymer including a cationic polymer which has potential for becoming positively charged. As another example, where the superabsorbent includes a cross-linked polymer that is generally cationic (e.g., includes about 75% or more by weight cationic polymer), so as to have a potential for becoming positively charged, the surface treatment, at least in part, includes a water-soluble, non-cross-linked polymer including an anionic polymer which has potential for becoming negatively charged.

In some embodiments, the commercially-available superabsorbent material (anionic polymers) may be surface-treated with a polyvinyl amine solution or other suitable solution to enhance the GBP value under 0.3 psi pressure. One example of a suitable polyvinyl amine solution is available from BASF Corporation in Mount Olive, N.J., under the trade name CATIOFAST® PR8106 (25 wt % solids). The polyvinyl amine solution can be dissolved in distilled water, to which the superabsorbent material may be added and stirred. After swelling, the superabsorbent material can be dried, such as at about 60 degrees Celsius for about 15 hours or longer. The dried superabsorbent material can be ground and screened through a sieve. The surface-treated superabsorbent material suitably contains between about 0.1% and about 10% by weight polyvinyl amine.

The absorbent composites may include between about 0% and about 75%, or between about 10% and about 70% by weight pulp fibers. In certain embodiments, the absorbent composites may include between about 5% and about 40% by weight pulp fibers. As illustrated in Example 2 below, the type and/or amount of pulp fibers in the absorbent composite may also affect the Composite Permeability of the absorbent composite. For example, when the superabsorbent material and the elastomeric material are held constant, and the ratios of superabsorbent material/elastomeric material/pulp fibers are also held constant, different types of pulp fibers are shown to affect the Composite Permeability. Furthermore, in general, the Composite Permeability may be increased by increasing the percentage of pulp fibers, particularly when simultaneously decreasing the percentage of elastomeric material.

The pulp fibers may include, but are not limited to, chemical pulps such as sulfite and sulfate (sometimes called Kraft) pulps, as well as mechanical pulps such as ground wood, thermomechanical pulp and chemithermomechanical pulp. More particularly, the pulp fibers may include cotton, typical wood pulps, cellulose acetate, rayon, thermomechanical wood pulp, chemical wood pulp, debonded chemical wood pulp, milkweed floss, and combinations thereof. Pulps derived from both deciduous and coniferous trees can be used. Additionally, the pulp fibers may include such hydrophilic materials as microcrystalline cellulose, microfibrillated cellulose, or any of these materials in combination with wood pulp fibers.

A surfactant may also be added to the absorbent composite to increase the wettability, or hydrophilicity, of the absorbent composite. Examples of suitable surfactants are commercially available from Uniqema in Wilmington, Del., under the trade designation AHCOVEL, and from Cognis Corporation in Cincinnati, Ohio, under the trade designation GLUCOPON 220.

The absorbent composite can be formed on a coform line. Coform processes combine separate polymer and additive streams into a single deposition stream in forming a nonwoven web. One example of such a process is disclosed in U.S. Pat. No. 4,100,324 to Anderson et al., which is hereby incorporated by reference in its entirety in a manner consistent with the present document. Another example of a suitable process for forming an absorbent composite is described in U.S. Pat. No. 5,350,624 to Georger et al., which is also hereby incorporated by reference in its entirety in a manner consistent with the present document.

One example of a method of forming the absorbent composite 20 is illustrated in FIG. 1. The dimensions of the apparatus in FIG. 1 are described herein by way of example. Other types of apparatus having different dimensions and/or different structures may also be used to form the absorbent composite 20. As shown in FIG. 1, elastomeric material 22 in the form of pellets can be fed through two pellet hoppers 24 into two single screw extruders 26 that each feed a spin pump 28. The elastomeric material 22 may be a multicomponent elastomer blend available under the trade designation KRATON® G2755 from Kraton Inc. of Houston, Tex. Each spin pump 28 feeds the elastomeric material 22 to a separate meltblown die 30. Each meltblown die 30 may have 30 holes per inch (hpi). The die angle may be adjusted anywhere between 0 and 70 degrees from horizontal, and is suitably set at about 45 degrees. The forming height may be at a maximum of about 16 inches, but this restriction may differ with different equipment.

A chute 32 having a width of about 24 inches wide may be positioned between the meltblown dies 30. The depth, or thickness, of the chute 32 may be adjustable in a range from about 0.5 to about 1.25 inches, or from about 0.75 to about 1.0 inch. A picker 34 connects to the top of the chute 32. The picker 34 is used to fiberize the pulp fibers 36. The picker 34 may be limited to processing low strength or debonded (treated) pulps, in which case the picker 34 may limit the illustrated method to a very small range of pulp types. In contrast to conventional hammermills that use hammers to impact the pulp fibers repeatedly, the picker 34 uses small teeth to tear the pulp fibers 36 apart. Suitable pulp fibers 36 for use in the method illustrated in FIG. 1 include Sulfatate HJ pulp, which is a short-fiber, low-strength, hardwood pulp available from Rayonier Corporation located in Jesup, Ga.

At an end of the chute 32 opposite the picker 34 is a superabsorbent material feeder 38. The feeder 38 pours superabsorbent material 40 into a hole 42 in a pipe 44 which then feeds into a blower fan 46. Past the blower fan 46 is a length of 4-inch diameter pipe 48 sufficient for developing a fully developed turbulent flow at about 5000 feet per minute, which allows the superabsorbent material 40 to become distributed. The pipe 48 widens from a 4-inch diameter to the 24-inch by 0.75-inch chute 32, at which point the superabsorbent material 40 mixes with the pulp fibers 36 and the mixture falls straight down and gets mixed on either side at an approximately 45-degree angle with the elastomeric material 22. The mixture of superabsorbent material 40, pulp fibers 36, and elastomeric material 22 falls onto a wire conveyor 50 moving from about 14 to about 35 feet per minute. However, before hitting the wire conveyor 50, a spray boom 52 sprays an aqueous surfactant mixture 54 in a mist through the mixture, thereby rendering the resulting absorbent composite 20 wettable. The surfactant mixture 54 may be a 1:3 mixture of GLUCOPON 220 UP and AHCOVEL Base N-62, available from Cognis Corp. and Uniqema, respectively. An under wire vacuum 56 is positioned beneath the conveyor 50 to assist in forming the absorbent composite 20.

The absorbent composite 20 can be incorporated into any suitable absorbent article. Examples of such suitable articles include personal care absorbent articles, such as diapers, diaper pants, baby wipes, training pants, absorbent underpants, child care pants, swimwear, sanitary napkins, wipes, menstrual pads, changing pads, menstrual pants, panty liners, panty shields, interlabials, tampons, tampon applicators, incontinence products, urinary shields, clothing components, bibs, shoe inserts, athletic and recreation products; health/medical absorbent articles such as products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads; household/industrial absorbent articles such as construction and packaging supplies, products for cleaning and disinfecting, wipes, covers, filters, towels, disposable cutting sheets, bath tissue, facial tissue, nonwoven roll goods, home-comfort products including pillows, pads, cushions, masks and body care products such as products used to cleanse or treat the skin, laboratory coats, cover-alls, trash bags, stain removers, topical compositions, laundry soil/ink absorbers, detergent agglomerators, lipophilic fluid separators; and the like. Absorbent composites of this invention can be used in either a single layer structure or a multi-layer structure, such as in a dual layer structure wherein the absorbent composite may serve as the upper layer, the lower layer, or both layers. For ease of explanation, the description hereafter will be in terms of a diaper.

Figure 2:
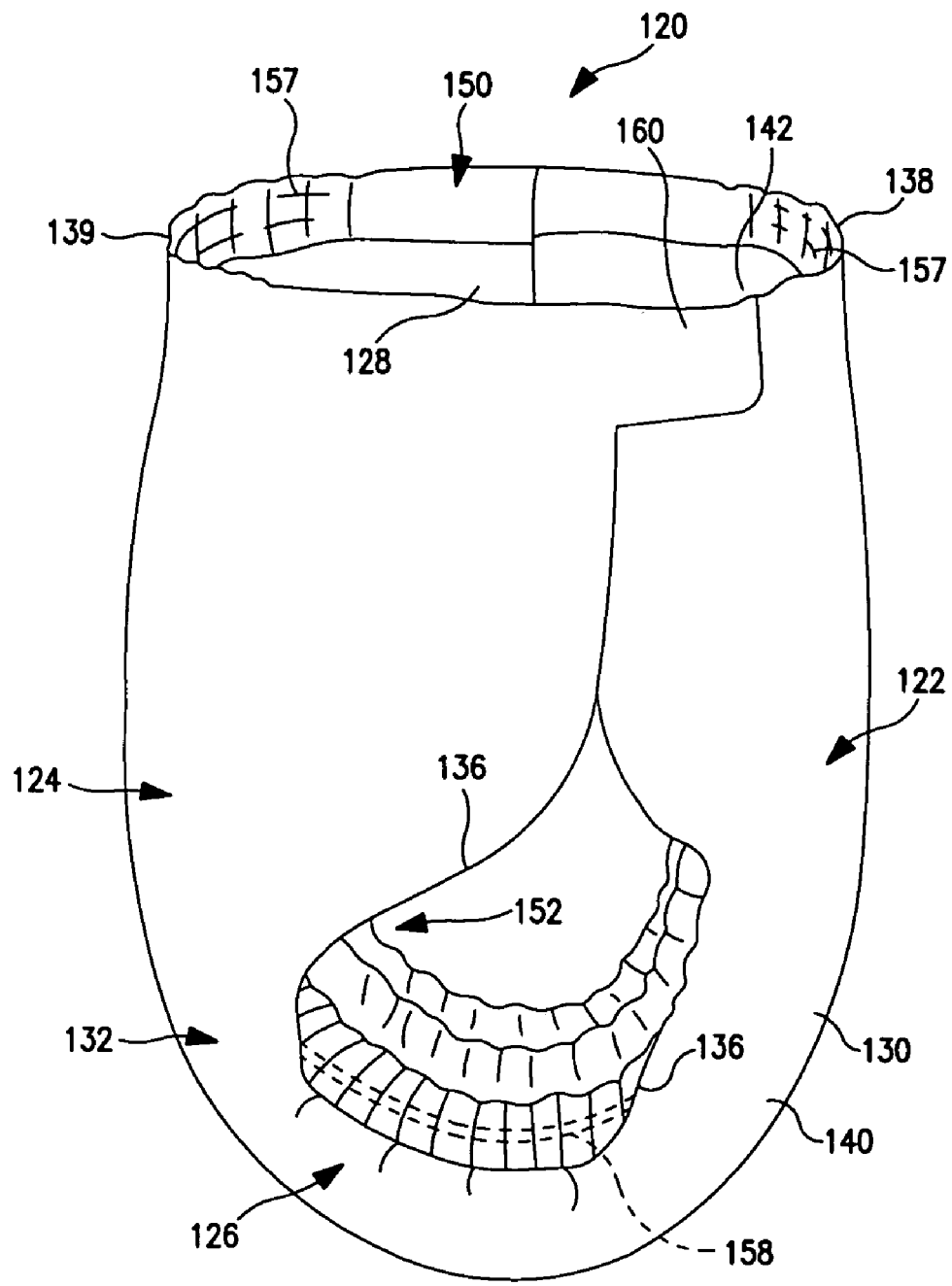
FIG. 2 is a perspective view of an absorbent article into which an absorbent composite may be incorporated.
Figure 3:
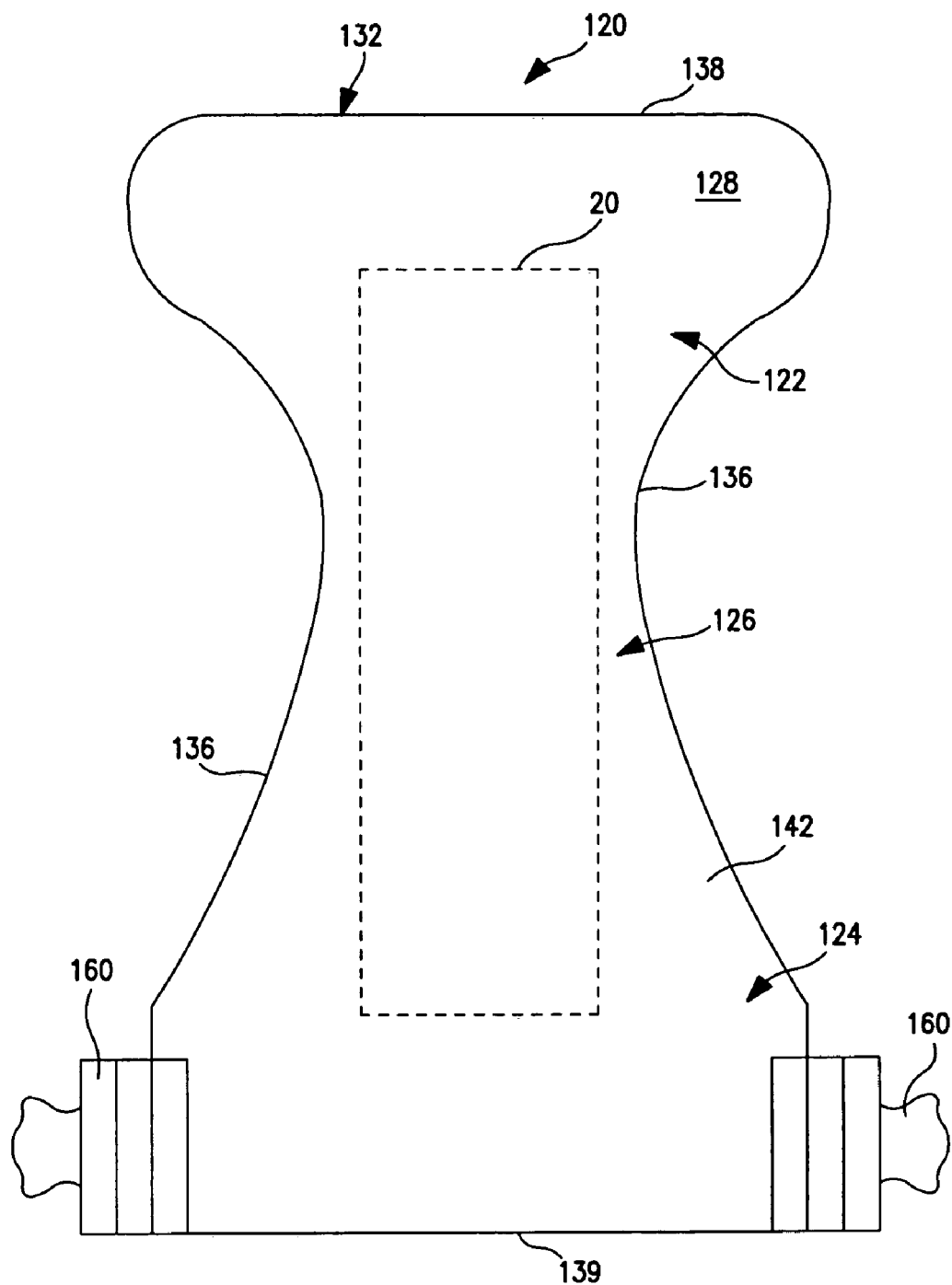
FIG. 3 is a plan view of an absorbent article with an absorbent composite incorporated therein, with the absorbent article in a stretched flat state and showing the body-contacting surface of the absorbent article.

An example of a suitable diaper 120 into which the absorbent composite 20 may be incorporated is illustrated in FIGS. 2 and 3. The diaper 120 includes a chassis 132. The chassis 132 defines a front region 122, a back region 124, a crotch region 126 interconnecting the front region 122 and the back region 124, a body-contacting surface 128 which is configured to contact the wearer, and an outer surface 130 opposite the body-contacting surface 128 which is configured to contact the wearer's clothing. The front region 122 is contiguous with a front waist edge 138, and the back region 124 is contiguous with a back waist edge 139.

The diaper 120 includes an outer cover 140, a body side liner 142 which is connected to the outer cover 140 in a superposed relation, and a pair of side panels 160 attached to the outer cover 140 and/or the body side liner 142. These side panels 160 can include tabs, straps, tearable seams, or similar devices that can be fastened between the front region 122 and the back region 124 by suitable means, including adhesives.

As shown in the diaper 120 in FIG. 2, the front and back regions 122 and 124 together define a three-dimensional pant configuration having a waist opening 150 and a pair of leg openings 152. The waist edges 138 and 139 of the chassis 132 are configured to encircle the waist of the wearer when worn and provide the waist opening 150 which defines a waist perimeter dimension. Portions of transversely opposed side edges 136 of the chassis 132 in the crotch region 126 generally define the leg openings 152. The front region 122 includes the portion of the diaper 120 which, when worn, is positioned on the front of the wearer while the back region 124 includes the portion of the diaper 120 which, when worn, is positioned on the back of the wearer. The crotch region 126 of the diaper 120 includes the portion of the diaper 120 which, when worn, is positioned between the legs of the wearer and covers the lower torso of the wearer. The side panels 160 of the diaper 120, when worn, are positioned forward from the hips of the wearer.

To enhance the containment of any body exudates discharged from the wearer, the chassis 132 can include a pair of elasticized containment flaps (not shown) which are configured to provide a barrier to the transverse flow of body exudates. The elasticized containment flaps define an unattached edge which assumes an upright, generally perpendicular configuration in at least the crotch region 126 of the diaper 120 to form a seal against the wearer's body. Suitable constructions and arrangements for the containment flaps are generally well known to those skilled in the art and are described in U.S. Pat. No. 4,704,116 issued Nov. 3, 1987 to Enloe, incorporated herein by reference in its entirety in a manner consistent with the present document.

To further enhance the containment of body exudates, the diaper 120 can include waist elastic members 157 and/or leg elastic members 158, as are known to those skilled in the art (FIG. 2). The waist elastic members 157 can be operatively joined to the outer cover 140 and/or the body side liner 142 along the opposite waist edges 138 and 139, and can extend over part or all of the waist edges. The leg elastic members 158 may be operatively joined to the outer cover 140 and/or the body side liner 142 longitudinally along the opposite side edges 136 and positioned in the crotch region 126 of the diaper 120.

The outer cover 140 may include a material that is substantially liquid-impermeable, and is suitably elastic, or at least stretchable, or in some cases may even be non-stretchable. The outer cover 140 can be a single layer of liquid-impermeable material, or may include a multi-layered laminate structure in which at least one of the layers is liquid-impermeable. For instance, the outer cover 140 can include a liquid-permeable outer layer and a liquid-impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid-permeable outer layer can be any suitable material such as one that provides a generally cloth-like texture. One example of such a material is a 20 gsm (grams per square meter) spunbond polypropylene nonwoven web. The outer layer may also be made of those materials of which liquid-permeable body side liner 142 is made. While it is not a necessity for the outer layer to be liquid-permeable, it is desired that it provides a relatively cloth-like texture to the wearer.

Another example of a suitable outer cover material is a 0.3 osy polypropylene spunbond that is necked 60% in a transverse direction and creped 60% in a longitudinal direction, laminated with 3 grams per square meter (gsm) Findley 2525A styrene-isoprene-styrene based adhesive to 8 gsm PEBAX® 2533 film with 20% TiO2 concentrate. The outer cover 140 can suitably be stretched, transversely and/or longitudinally, by at least 50% (to at least 150% of an initial (unstretched) width and/or length of the outer cover 140).

Yet another example of a suitable material for the outer cover 140 is a breathable elastic film/nonwoven laminate, described in U.S. Pat. No. 5,883,028, issued to Morman et al., which is hereby incorporated by reference in its entirety in a manner consistent with the present document. Examples of materials having two-way stretchability and retractability are disclosed in U.S. Pat. No. 5,116,662 issued to Morman and U.S. Pat. No. 5,114,781 issued to Morman, both of which are also hereby incorporated by reference in their entireties in a manner consistent with the present document. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The inner layer of the outer cover 140 can be both liquid and vapor-impermeable, or can be liquid-impermeable and vapor-permeable. The inner layer may be manufactured from a thin plastic film, although other flexible liquid-impermeable materials may also be used. The inner layer, or the liquid-impermeable outer cover 140 when a single layer, prevents waste material from wetting articles, such as bedsheets and clothing, as well as the wearer and care giver. A suitable liquid-impermeable film for use as a liquid-impermeable inner layer, or a single layer liquid-impermeable outer cover 140, is a 0.02 millimeter polyethylene film commercially available from Huntsman Packaging of Newport News, Va., U.S.A. If the outer cover 140 is a single layer of material, it can be embossed and/or matte finished to provide a more cloth-like appearance. As earlier mentioned, the liquid-impermeable material can permit vapors to escape from the interior of the disposable absorbent article, while still preventing liquids from passing through the outer cover 140. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid-permeable body side liner 142 is illustrated as overlying the outer cover 140 and absorbent composite 20, and may but need not have the same dimensions as the outer cover 140. The body side liner 142 is desirably compliant, soft feeling, and non-irritating to the wearer's skin, and may be stretchable or elastomeric. Further, the body side liner 142 can be less hydrophilic than the absorbent composite 20, to present a relatively dry surface to the wearer and permit liquid to readily penetrate through its thickness.

The body side liner 142 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 142. For example, the body side liner 142 can be composed of a meltblown or spunbonded web of polyolefin fibers. The body side liner 142 can also be a bonded-carded web composed of natural and/or synthetic fibers, or a neck-stretched/creped spunbond. The body side liner 142 can be composed of a substantially hydrophobic material, and the hydrophobic material can, optionally, be treated with a surfactant or otherwise processed to impart a desired level of wettability and hydrophilicity.

The absorbent composite 20 can be positioned or located between the outer cover 140 and the body side liner 142, which components can be joined together by any suitable means, such as adhesives, as are well known in the art. FIG. 3 illustrates the diaper 120 with the absorbent composite 20 incorporated therein.

The chassis 132 can also incorporate other materials that are designed primarily to receive, temporarily store, and/or transport liquid along the mutually facing surface with the absorbent composite, thereby maximizing the overall absorbent capacity of the absorbent composite 20, if desired. One suitable material is referred to as a surge layer (not shown) and includes a material having a basis weight of about 50 to about 120 grams per square meter (gsm), and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A. Another example of a suitable surge layer may include a material made of 6 denier polyethylene terephthalate (PET) and 6 denier bicomponent binder fiber, having a basis weight of about 50 to about 120 gsm.

The various components of the diaper 120 can be integrally assembled together employing various types of suitable attachment means, such as adhesive, ultrasonic and thermal bonds or combinations thereof.

As described herein, the absorbent composite of the invention includes carefully chosen superabsorbent material, elastomeric material, and, optionally, pulp fibers, all present in specific ratios to achieve an absorbent composite that has a Composite Stretchability of about 50% or more, and a Composite Permeability of about 15 Darcy or more. Another absorbent composite of the invention including about 60 weight percent or more of superabsorbent, elastomeric material, and, optionally, pulp fibers, has a Composite Stretchability of about 30% or more and a Composite Permeability of about 15 Darcy or more. Yet another absorbent composite of the invention including superabsorbent material, elastomeric material, and, optionally, pulp fibers, has a Composite Stretchability of about 100% or more, and a Composite Permeability of about 10 Darcy or more. Additionally, the absorbent composite has improved superabsorbent containment compared to conventional superabsorbent-containing absorbent composites. The absorbent composite of the invention provides better fit, greater comfort, and improved fluid handling characteristics in a variety of absorbent articles, compared to conventional absorbent composites.

In general, stretchability of an absorbent composite is largely dependent upon the amount of elastomeric material in the absorbent composite. The higher the amount of elastomeric material, the higher the stretchability of the absorbent composite is. On the other hand, stretchability is significantly reduced when fluff fiber amount is increased. Permeability is partly dependent on the superabsorbent materials GBP value as well as amount of superabsorbent material in the absorbent composite.

As mentioned above, structural factors also affect stretchability and permeability of an absorbent composite, such as fiber size and length of elastomeric material, number of bonds formed and binding strength, basis weight and density of absorbent composite, defects, and the like. The fiber size and length of elastomeric material are determined by melt spinning technologies used (i.e., meltblown or spunbond). Two structural variables which often do not depend on fiber spinning technologies are basis weight and density of an absorbent composite. Basis weight of an absorbent composite suitable for this invention can range from about 100 to about 1,000 grams per square meter, or from about 200 to about 800 grams per square meter, for a single layered composite. Multiple layers can be used in order to achieve high total basis weight. Density range of absorbent composites of this invention may range from about 0.05 to about 0.5 gram per cubic centimeter, or from about 0.1 to about 0.3 gram per cubic centimeter. Post densification treatment can be applied if a higher density is needed.

TEST METHODS

Composite Stretchability Testing

To determine the stretchability of a material, three predetermined stretch ratios are chosen: 30%, 50%, and 100%. Each material is first tested at 30%, then at 50% if the material has passed the 30% test, and finally at 100% if the material has passed both the 30% and the 50% tests. For each level of stretchability testing, three specimens are tested and all three must pass in order to consider the sample as having the respective level of stretchability. Each specimen is tested only once, even if the specimen is not damaged.

The stretchability of a composite is measured after 3 cycles of stretching to a predetermined ratio of extension and releasing, thereby allowing the stretched composite to retract back to its original dimension.

Stretchability is defined according to the following equation:

$$\text{Stretchability} = (L_e - L_o) \times 100\% / L_o$$

wherein $L_e$ is the length after extension (i.e., the predetermined ratio), and $L_o$ is the original sample length. For a sample to be qualified as having a predetermined stretchability, the sample must be able to demonstrate all of the following requirements:

(1) The sample must be able to reach the predetermined stretch ratio.

(2) The sample must be able to retract at least 80% of the extension when the force is removed within a 1-minute interval. The retraction is defined as:

$$\text{Retraction} = \{1 - (L_f - L_o)/(L_e - L_o)\} \times 100\%$$

wherein $L_f$ is the sample length after the force is released for 1 minute, $L_e$ is the length after extension (i.e., the predetermined ratio), and $L_o$ is the original sample length before extension.

(3) The sample must meet the first criterion after the second and third extension, and the second criterion after the third extension on the same specimen. (In carrying out the test, retraction criterion is only checked after the third extension).

(4) The sample must not show apparent structure changes, such as no visible voids, cracks, or defects generated compared to the original sample.

The absorbent composite was cut into 3-inch by 7-inch specimens. INSTRON 4443, available form Instron Corporation of Carton, Mass., was used to measure stretchability. Each specimen was mounted onto the equipment vertically with two clamps and the locations of the clamps were marked on the specimen. The distance between the two clamps was 4 inches ($L_o$). The specimen was stretched by moving the upper clamp upward at a rate of 500 mm/min and held for 5 seconds at the predetermined length of extension ($L_e$). After 5 seconds of holding, the upper clamp was returned to the original position and the specimen was free to retract. The second cycle of stretching was started after the upper clamp was back in the original position for 10 seconds, followed by the third cycle. The stretching and retraction procedure for the second and third cycles was the same as the first cycle. The specimen was removed from the equipment after completion of the third stretching cycle and laid on the bench. The distance between the two marks ($L_f$) was measured after the specimen was relaxed for 1 minute. Each absorbent composite was stretched in both the machine direction (MD) and the cross-machine direction (CD). The lower stretchability value measured from the CD and MD directions was chosen to represent stretchability of the absorbent composite.

Centrifuge Retention Capacity (CRC) Test

The Centrifuge Retention Capacity (CRC) Test measures the ability of the superabsorbent material to retain liquid therein after being saturated and subjected to centrifugation under controlled conditions. The resultant retention capacity is stated as grams of liquid retained per gram weight of the sample (g/g). The sample to be tested is prepared from particles which are prescreened through a U.S. standard 30 mesh screen and retained on a U.S. standard 50 mesh screen. As a result, the sample comprises particles sized in the range of about 300 to about 600 microns. The particles can be prescreened by hand or automatically and are stored in a sealed airtight container until testing.

The retention capacity is measured by placing 0.2±0.005 grams of the prescreened sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat-sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is placed in the pouch, the remaining open edge of the pouch is also heat-sealed. Empty bags are also made to serve as controls. Three samples (e.g., filled and sealed bags) are prepared for the test. The filled bags must be tested within three minutes of preparation unless immediately placed in a sealed container, in which case the filled bags must be tested within thirty minutes of preparation.

The bags are placed between two TEFLON® coated fiberglass screens having 3 inch openings (Taconic Plastics, Inc., Petersburg, N.Y.) and submerged in a pan of the test solution at 23 degrees Celsius, making sure that the screens are held down until the bags are completely wetted. After wetting, the samples remain in the solution for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the retention capacity is determined as:

$$\frac{\text{Sample \& bag weight after centrifuge} - \text{empty bag weight after centrifuge} - \text{dry sample weight}}{\text{dry sample weight}}$$

The three samples are tested and the results are averaged to determine the retention capacity (CRC) of the superabsorbent material. The samples are tested at 23±1 degrees Celsius at 50±2 percent relative humidity.

Gel Bed Permeability (GBP)@0.3 psi Swell Pressure Test

As used herein, the Gel Bed Permeability (GBP) Under Load Test, otherwise referred to herein as GBP at 0.3 psi, determines the permeability of a swollen bed of gel particles (e.g., the superabsorbent material or the absorbent composite), under conditions that are commonly referred to as being "under load" conditions. The term "under load" means that swelling of the particles is restrained by a load generally consistent with normal usage loads applied to the particles, such as sitting, walking, twisting, etc. by the wearer.

Figure 4:
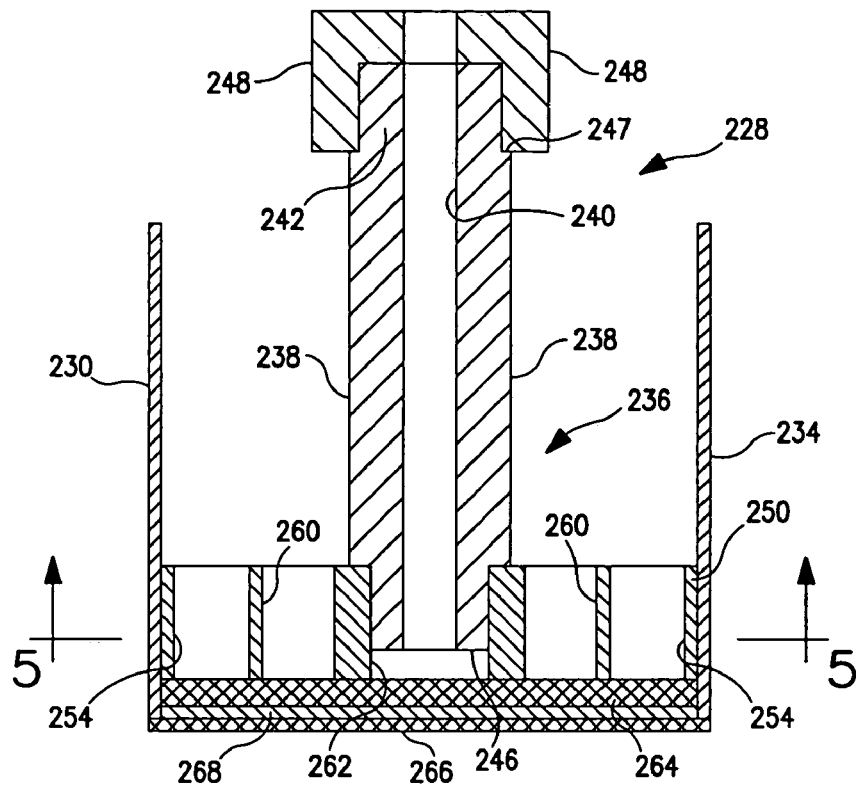
FIG. 4 depicts apparatus used to measure permeability of either free-flowing particles or absorbent composites.
Figure 5:
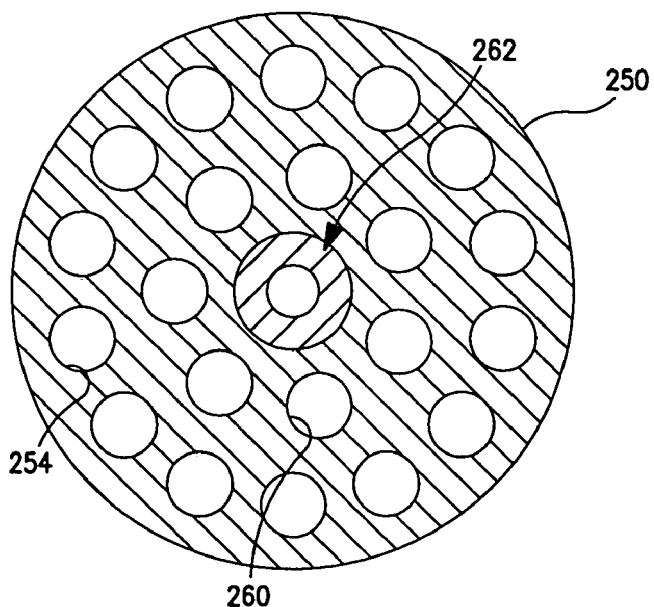
FIG. 5 depicts a bottom view of the apparatus of FIG. 4.

A suitable apparatus for conducting the Gel Bed Permeability Test is shown in FIGS. 4 and 5 and indicated generally at 228. The test apparatus 228 comprises a sample container, generally indicated at 230, and a piston, generally indicated at 236. The piston 236 comprises a cylindrical LEXAN shaft 238 having a concentric cylindrical hole 240 bored down the longitudinal axis of the shaft. Both ends of the shaft 238 are machined to provide upper and lower ends respectively designated 242, 246. A weight, indicated as 248, rests on one end 242 and has a cylindrical hole a bored through at least a portion of its center.

A circular piston head 250 is positioned on the other end 246 and is provided with a concentric inner ring of seven holes 260, each having a diameter of about 0.95 cm, and a concentric outer ring of fourteen holes 254, also each having a diameter of about 0.95 cm. The holes 254, 260 are bored from the top to the bottom of the piston head 250. The piston head 250 also has a cylindrical hole 262 bored in the center thereof to receive end 246 of the shaft 238. The bottom of the piston head 250 may also be covered with a biaxially stretched 100 mesh stainless steel screen 264.

The sample container 230 comprises a cylinder 234 and a 400 mesh stainless steel cloth screen 266 that is biaxially stretched to tautness and attached to the lower end of the cylinder. A gel particle sample, indicated as 268 in FIG. 4, is supported on the screen 266 within the cylinder 234 during testing.

The cylinder 234 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 10 cm. Drainage holes (not shown) are formed in the sidewall of the cylinder 234 at a height of approximately 7.8 cm above the screen 266 to allow liquid to drain from the cylinder to thereby maintain a fluid level in the sample container at approximately 7.8 cm above the screen 266. The piston head 250 is machined from a LEXAN rod or equivalent material and has a height of approximately 16 mm and a diameter sized such that it fits within the cylinder 234 with minimum wall clearance but still slides freely. The shaft 238 is machined from a LEXAN rod or equivalent material and has an outer diameter of about 2.22 cm and an inner diameter of about 0.64 cm.

The shaft upper end 242 is approximately 2.54 cm long and approximately 1.58 cm in diameter, forming an annular shoulder 247 to support the weight 248. The annular weight 248 has an inner diameter of about 1.59 cm so that it slips onto the upper end 242 of the shaft 238 and rests on the annular shoulder 247 formed thereon. The annular weight 248 can be made from stainless steel or from other suitable materials resistant to corrosion in the presence of the test solution, which is 0.9 weight percent sodium chloride solution in distilled water. The combined weight of the piston 236 and annular weight 248 equals approximately 596 grams (g), which corresponds to a pressure applied to the sample 268 of about 0.3 pounds per square inch (psi), or about 20.7 dynes/cm$^2$ (2.07 kPa), over a sample area of about 28.27 cm$^2$.

When the test solution flows through the test apparatus during testing as described below, the sample container 230 generally rests on a 16 mesh rigid stainless steel support screen (not shown). Alternatively, the sample container 230 may rest on a support ring (not shown) diametrically sized substantially the same as the cylinder 234 so that the support ring does not restrict flow from the bottom of the container.

To conduct the Gel Bed Permeability Test under "free swell" conditions, the piston 236, with the weight 248 seated thereon, is placed in an empty sample container 230 and the height is measured using a suitable gauge accurate to 0.01 mm with the platen removed. It is important to measure the height of each sample container 230 empty and to keep track of which piston 236 and weight 248 is used when using multiple test apparatus. The same piston 236 and weight 248 should be used for measurement when the sample 268 is later swollen following saturation.

The sample to be tested is prepared from particles which are prescreened through a U.S. standard 30 mesh screen and retained on a U.S. standard 50 mesh screen. As a result, the test sample comprises particles sized in the range of about 300 to about 600 microns. The particles can be prescreened by hand or automatically. Also test samples can be as-is particles. Approximately 0.9 grams of the sample is placed in the sample container 230 and spread out evenly on the bottom of the sample container 230. The sample container 230, with 0.9 grams of sample in it, and with the piston 236 and weight 248 placed on the sample within the sample container 230, is then submerged in the test solution for a time period of about 60 minutes to saturate the sample.

At the end of this period, the sample container 230, piston 236, weight 248, and sample 268 are removed from the solution. The thickness of the saturated sample 268 is determined by again measuring the height from the bottom of the weight 248 to the top of the cylinder 234, using the same thickness gauge used previously provided that the zero point is unchanged from the initial height measurement. The height measurement obtained from measuring the empty sample container 230, piston 236, and weight 248 is subtracted from the height measurement obtained after saturating the sample 268. The resulting value is the thickness, or height "H" of the swollen sample.

The permeability measurement is initiated by delivering a flow of the test solution into the sample container 230 with the saturated sample 268, piston 236, and weight 248 inside. The flow rate of test solution into the sample container 230 is adjusted to maintain a fluid height of about 7.8 cm above the bottom of the sample container 230. The quantity of solution passing through the sample 268 versus time is measured gravimetrically. Data points are collected every second for at least twenty seconds once the fluid level has been stabilized to and maintained at about 7.8 cm in height. The flow rate Q through the swollen sample 268 is determined in units of grams/second (g/s) by a linear least-square fit of fluid passing through the sample 268 (in grams) versus time (in seconds).

Permeability in cm$^2$ is obtained by the following equation:

$$K = [Q*H*\mu]/[A*\rho*P]$$

where K=Permeability (cm$^2$), Q=flow rate (g/sec), H=height of sample (cm), $\mu$=liquid viscosity (poise) (approximately one centipoises for the test solution used with this Test), A=cross-sectional area for liquid flow (cm$^2$), $\rho$=liquid density (g/cm$^3$) (approximately one g/cm$^3$, for the test solution used with this Test) and P=hydrostatic pressure (dynes/cm$^2$) (normally approximately 3,923 dynes/cm$^2$). The hydrostatic pressure is calculated from $$P = \rho*g*h$$

where $\rho$=liquid density (g/cm$^3$), g=gravitational acceleration, nominally 981 cm/sec$^2$, and h=fluid height, e.g., 7.8 cm for the Gel Bed Permeability Test described herein.

A minimum of three samples is tested and the results are averaged to determine the gel bed permeability of the sample.

Composite Permeability Test Method

The Composite Permeability Test is used to determine the permeability of the absorbent composite, and more particularly a "z-direction" permeability of the absorbent composite based on liquid flow through the thickness of the composite. This test is substantially similar to the Gel Bed Permeability Test set forth above, with the following noted exceptions. Referring back to FIGS. 4 and 5, instead of being swelled under a 0.3 psi pressure, the absorbent composites were swelled under no load but tested their permeability under a 0.3 psi pressure (the piston 236 and weight 248 were placed onto the absorbent composite after it was freely saturated for 60 minutes in a 0.9 weight percent NaCl saline solution). Also, instead of particulate superabsorbent material being placed in the sample container 230, a circular absorbent composite sample 268 (e.g., either formed or otherwise cut from a larger absorbent composite), with any forming material wrap (e.g., forming tissue) removed and having a diameter of about 6 cm is placed in the sample container 230 at the bottom of the cylinder 234 in contact with the screen 264. The sample container 230 (without the piston and weight therein) is then submerged in a 0.9 weight percent NaCl saline solution for a time period of about 60 minutes to saturate the absorbent composite. The same height measurement obtained for the GBP Test are taken, e.g., with the sample container 230 empty and with the absorbent composite sample within the sample container 230 and saturated.

The absorbent composite permeability measurement is initiated by delivering a continuous flow of saline solution into the sample container 230 with the saturated absorbent composite, the piston 236, and the weight 248 inside. The saline solution is delivered to the sample container 230 at a flow rate sufficient to maintain a fluid height of about 7.8 cm above the bottom of the sample container 230. The quantity of fluid passing through the absorbent composite versus time is measured gravimetrically. Data points are collected every second for at least twenty seconds once the fluid level has been stabilized to and maintained at about 7.8 cm in height. The flow rate Q through the absorbent composite sample 268 is determined in units of grams/second (g/s) by a linear least-square fit of fluid passing through the sample container 230 (in grams) versus time (in seconds). The permeability of the absorbent composite is then determined using the equation set forth above for the Gel Bed Permeability Test.

Where the Absorbent Composite Permeability Test is conducted as described above, and more particularly where the absorbent composite sample is submerged in the solution without the piston and weight thereon, the test is said to be conducted under "free swell" conditions whereby the absorbent composite is allowed to swell free of any restraining load. In a variation of this test, the piston and weight may be placed on the sample within the sample container 230 and then the entire assembly can be submerged so that a load is applied to the sample as the sample becomes saturated and swells. When conducted in this manner the test is referred to as being conducted "under load."

EXAMPLES

Example 1

In this example, the Composite Permeability of five different absorbent composite samples, each including different superabsorbent materials, was measured and compared. The other components in the absorbent composite samples remained constant among the samples, with only the type of superabsorbent material (SAM) varying among the samples.

The SAM in Sample 1 was SXM 9543, commercially available from Degussa Superabsorber of Greensboro, N.C., surface-treated with a polyvinyl amine solution available from BASF Corporation in Mount Olive, N.J., under the trade name CATIOFAST® PR8106 (25 wt % solids). The polyvinyl amine solution was pre-dissolved into distilled water, and dry SXM 9543 superabsorbent was added into the solution and stirred. The SXM 9543 swelled to about 2.5 g/g levels (for example, 30 grams of dry superabsorbent were treated with a solution including 3 grams of CATIOFAST® PR8106 and 72.75 grams of distilled water) in the prepared polyvinyl amine solution and was then dried at 60 degrees Celsius for 15 hours. The dried superabsorbent was ground by an Osterizer® blender at high speed at the setting of "blend" and screened through an 850 micron sieve. The surface-treated SXM 9543 contained about 2.5% by weight polyvinyl amine.

The SAM in Sample 2 was untreated SXM 9543.

The SAM in Sample 3 was SXM 9394, also commercially available from Degussa Superabsorber.

The SAM in Sample 4 was FAVOR® 880, also available from Degussa Superabsorber.

The SAM in Sample 5 was 2035HP, commercially available from Dow Chemical Co. in Midland, Mich.

In each sample, the ratio of SAM/elastic material/pulp fibers was 75/15/10. The elastic material was KRATON® G 2755, available from Kraton Inc. of Houston, Tex. The pulp fibers were Sulfatate HJ, available from Rayonier Inc. of Jesup, Ga.

Composite Permeability and stretchability were tested using the test ds described herein. All composites in Tables 1 and 2 had a basis weight of 425 per square meter and a density of 0.27 gram per cubic centimeter.

TABLE 1

Composite Stretchability and Permeability Test Results

| Sample | SAM Type | SAM Property CRC (g/g) | SAM Property GBP under 0.3 psi swell (Darcy) | SAM/ KRATON/ Pulp Ratio | Permeability (Darcy) | Stretchability (%) |
|---|---|---|---|---|---|---|
| 1 | PVAm-9543 (2.5% level) | 22 | 44.5 | 75/15/10 | 24.5 | 100 |
| 2 | SXM 9543 | 23 | 14.5 | 75/15/10 | 2.5 | 100 |
| 3 | SXM 9394 | 27 | 4.5 | 75/15/10 | 3.2 | 100 |
| 4 | FAVOR ® 880 | 31 | 1.5 | 75/15/10 | 0.5 | 100 |
| 5 | 2035 HP | 26 | 1.5 | 75/15/10 | 4.2 | 100 |

As shown in Table 1, the SAM with higher GBP values is helpful for improving Composite Permeability. All samples demonstrated the requisite stretchability of the invention, but only Sample 1, which exhibited the requisite Composite Permeability, fell within the scope of the invention.

Example 2

Besides the SAM GBP, the Composite Permeability also depends on the of SAM/elastomeric material/pulp fibers. This example shows that when the percentage of pulp fibers increases, or when the percentage of elastomeric material decreases, the Composite Permeability will consequently increase.

Table 2 includes 10 absorbent composite samples varying in terms of SAM type, pulp type, and/or ratios of SAM/elastomeric material/pulp fibers. The same types of SAM and elastomeric material used in Example 1 were used in this example. The types of pulp fiber used in this example were NF 405, available from Weyerhaeuser of Federal Way, Wash.; Sulfatate-H-J ("SHJ"), available from Rayonier of Jesup, Ga.; and CR 1654, available from Bowater of Coosa Pines, Ala.

strated a combination of Composite Stretchability of 30% or more and Composite Permeability of 15 Darcy while it contains at least 60 weight percent of superabsorbent. Samples 1, 7, and 13 demonstrated a combination of Composite Stretchability of 100% or more and Composite Permeability of 10 Darcy or more. None of the other samples which included superabsorbent with low GBP values demonstrated these combinations of Composite Stretchability and Composite Permeability values.

In Table 2, Samples 14 and 15 contain only SAM and pulp fibers and were produced according to current diaper manu-

TABLE 2

Composite Stretchability and Permeability Test Results

| Sample | SAM Type | SAM/KRATON/Pulp ratio | Pulp type | Permeability (Darcy) | Stretchability (%) |
|---|---|---|---|---|---|
| 6 | PVAm-9543 (2.5% level) | 30/10/60 | NF405 | 35.8 | <30 |
| 7 | PVAm-9543 (2.5% level) | 75/25/0 | NA | 12.7 | 100 |
| 8 | SXM 9543 | 50/10/40 | NF405 | 18.4 | 30 |
| 9 | SXM 9543 | 75/15/10 | NF405 | 3.1 | 100 |
| 10 | SXM 9543 | 50/10/40 | SHJ | 11.0 | 50 |
| 11 | SXM 9394 | 50/15/35 | SHJ | 8.0 | 50 |
| 12 | SXM 9543 | 50/15/35 | SHJ | 8.7 | 50 |
| 13 | PVAm-9543 (2.5% level) | 70/25/5 | NF405 | 11.0 | 100 |
| 14 | SXM 9543 | 50/0/50 | CR1654 | 25.3 | 0 |
| 15 | SXM 9394 | 50/0/50 | CR1654 | 22.8 | 0 |

By changing the ratios of SAM/elastomeric material/pulp fibers or using different pulp fibers, some of the absorbent composites in Table 1 that meet the minimum requisite Composite Permeability, such as Sample 1, were now unable to reach the stretchability target, as in Sample 6. In Table 2, Samples 8 and 9 both included NF 405 pulp, but different ratios of SAM/elastomeric material/pulp fibers. Consequently, Sample 8 exhibits a higher permeability and a lower stretchability while Sample 9 exhibits the opposite.

When SAM and elastic material types as well as ratios of SAM/elastomeric material/pulp fibers remain constant, different types of pulp fibers also affect the Composite Permeability. In Table 2, Samples 8 and 10 use different types of pulp fibers and exhibit different combinations of permeability and stretchability.

The stretchability of a stretchable absorbent composite depends largely on the types of elastic polymers and the percentage of elastic polymers in the composite. In general, as the percentage of an elastic polymer increases, stretchability of a stretchable absorbent composite increases, and vice versa. In Table 2, Sample 6 has Composite Permeability values within the parameters of the invention, but its stretchability value falls outside the parameters of the invention. Therefore, Sample 6 is not considered to be within the scope of the invention.

Though fluff type has a slight effect on composite permeability, superabsorbent GBP plays a much more important role in this aspect. All samples that demonstrated the requisite stretchability and permeability of the invention include polyvinyl amine surface-treated SXM 9543 superabsorbent which has a GBP under 0.3 psi swell value of greater than 30 Darcy. Among these samples, Sample 1 demonstrated a combination of Composite Stretchability of 50% or more and Composite Permeability of 15 Darcy or more. Sample 1 also demonfacturing processes, which do not contain any elastic polymers and exhibit 0% stretchability. Samples 14 and 15 are provided for reference.

Samples 1-15 in Examples 1 and 2 demonstrate the importance of the selection of suitable SAMs, elastic materials, pulp types, and the balanced ratios of materials involved in producing a stretchable absorbent composite having properties defined by the invention.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A stretchable absorbent composite, comprising: a superabsorbent material; and an elastomeric material; wherein the absorbent composite exhibits a Composite Stretchability of about 50% or more, and a Composite Permeability of about 15 Darcy or more; wherein the absorbent composite is located within a personal care absorbent article.

2. The absorbent composite of claim 1, comprising between about 5% and about 95% by weight superabsorbent material.

3. The absorbent composite of claim 1, comprising between about 50% and about 95% by weight superabsorbent material.

4. The absorbent composite of claim 1, comprising between about 5% and about 25% by weight elastomeric material.

5. The absorbent composite of claim 1, further comprising between 0% and about 75% by weight pulp fibers.

6. The absorbent composite of claim 1, further comprising a surfactant.

7. The absorbent composite of claim 1, wherein the superabsorbent material has a gel bed permeability under 0.3 psi of about 30 Darcy or more.

8. The absorbent composite of claim 1, wherein the superabsorbent material has a Centrifuge Retention Capacity of about 20 grams/gram or more.

9. The absorbent composite of claim 1, wherein the superabsorbent material comprises an anionic superabsorbent material surface-treated with a polyvinyl amine solution.

10. The absorbent composite of claim 1, wherein the elastomeric material comprises at least one of the group consisting of olefinic copolymers, polyethylene elastomers, polypropylene elastomers, polyester elastomers, ethylene-propylene-diene terpolymers, styrene-isoprene-styrene, styrene-butadiene-styrene, styrene-isoprene-butadiene-styrene, styrene-ethylene/butylene-styrene, styrene-ethylene/propylene-styrene, polyurethane, polyisoprene, cross-linked polybutadiene, and combinations thereof.

11. A stretchable absorbent composite, comprising: about 60% by weight or more superabsorbent material; and an elastomeric material; wherein the absorbent composite exhibits a Composite Stretchability of about 30% or more, and a Composite Permeability of about 15 Darcy or more; wherein the absorbent composite is located within a personal care absorbent article.

12. The absorbent composite of claim 11, comprising between about 5% and about 25% by weight elastomeric material.

13. The absorbent composite of claim 11, further comprising between 0% and about 25% by weight pulp fibers.

14. The absorbent composite of claim 11, further comprising a surfactant.

15. The absorbent composite of claim 11, wherein the superabsorbent material has a gel bed permeability under 0.3 psi of about 30 Darcy or more.

16. The absorbent composite of claim 11, wherein the superabsorbent material has a Centrifuge Retention Capacity of about 20 grams/gram or more.

17. The absorbent composite of claim 11, wherein the superabsorbent material comprises an anionic polymer superabsorbent material surface-treated with a polyvinyl, amine solution.

18. The absorbent composite of claim 11, wherein the elastomeric material comprises at least one of the group consisting of olefinic copolymers, polyethylene elastomers, polypropylene elastomers, polyester elastomers, ethylene-propylene-diene terpolymers, styrene-isoprene-styrene, styrene-butadiene-styrene, styrene-isoprene-butadiene-styrene, styrene-ethylene/butylene-styrene, styrene-ethylene/propylene-styrene, polyurethane, polyisoprene, cross-linked polybutadiene, and combinations thereof.

19. A stretchable absorbent composite, comprising: a superabsorbent material; and an elastomeric material; wherein the absorbent composite exhibits a Composite Stretchability of about 100% or more, and a Composite Permeability of about 10 Darcy or more; wherein the absorbent composite is located within a personal care absorbent article.

20. The absorbent composite of claim 19, comprising between about 5% and about 95% by weight superabsorbent material.

21. The absorbent composite of claim 19, comprising between about 50% and about 95% by weight superabsorbent material.

22. The absorbent composite of claim 19, comprising between about 5% and about 25% by weight elastomeric material.

23. The absorbent composite of claim 19, further comprising between 0% and about 75% by weight pulp fibers.

24. The absorbent composite of claim 19, further comprising a surfactant.

25. The absorbent composite of claim 19, wherein the superabsorbent material has a gel bed permeability under 0.3 psi of about 30 Darcy or more.

26. The absorbent composite of claim 19, wherein the superabsorbent material has a Centrifuge Retention Capacity of about 20 grams/gram or more.

27. The absorbent composite of claim 19, wherein the superabsorbent material comprises an anionic polymer superabsorbent material surface-treated with a polyvinyl amine solution.

28. The absorbent composite of claim 19, wherein the elastomeric material comprises at least one of the group consisting of olefinic copolymers, polyethylene elastomers, polypropylene elastomers, polyester elastomers, ethylene-propylene-diene terpolymers, styrene-isoprene-styrene, styrene-butadiene-styrene, styrene-isoprene-butadiene-styrene, styrene-ethylene/butylene-styrene, styrene-ethylene/propylene-styrene, polyurethane, polyisoprene, cross-linked polybutadiene, and combinations thereof.

29. A diaper comprising the absorbent composite of claim 1.

30. A diaper comprising the absorbent composite of claim 11.

31. A diaper comprising the absorbent composite of claim 19.

* * * * *

UNITED STATES PATENT AND TRADEMARK OFFICE
CERTIFICATE OF CORRECTION

PATENT NO. : 7,662,745 B2 Page 1 of 1
APPLICATION NO. : 10/739385
DATED : February 16, 2010
INVENTOR(S) : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1179 days.

Signed and Sealed this

Twenty-eighth Day of December, 2010

David J. Kappos
*Director of the United States Patent and Trademark Office*